(12) United States Patent
Wang et al.

(10) Patent No.: US 11,913,042 B2
(45) Date of Patent: Feb. 27, 2024

(54) METHODS FOR PREPARING AND USING HIGHLY ACTIVE BLOOD COAGULATION FACTOR XI MUTANT AND GENE THERAPY/EDITING VECTOR AND RECOMBINANT/FUSION PROTEIN THEREOF

(71) Applicants: RUIJIN HOSPITAL SHANGHAI JIAOTONG UNIVERSITY SCHOOL OF MEDICINE, Shanghai (CN); Xuefeng Wang, Shanghai (CN); Wenman Wu, Shanghai (CN); Qiulan Ding, Shanghai (CN)

(72) Inventors: Xuefeng Wang, Shanghai (CN); Wenman Wu, Shanghai (CN); Qiulan Ding, Shanghai (CN)

(73) Assignees: RUIJIN HOSPITAL SHANGHAI JIAOTONG UNIVERSITY SCHOOL OF MEDICINE, Shanghai (CN); Wenman Wu, Shanghai (CN); Xuefeng Wang, Shanghai (CN); Qiulan Ding, Shanghai (CN)

( * ) Notice: Subject to any disclaimer, the term of this patent is extended or adjusted under 35 U.S.C. 154(b) by 931 days.

(21) Appl. No.: 16/771,700

(22) PCT Filed: Aug. 30, 2018

(86) PCT No.: PCT/CN2018/103201
§ 371 (c)(1),
(2) Date: Jun. 11, 2020

(87) PCT Pub. No.: WO2019/114324
PCT Pub. Date: Jun. 20, 2019

(65) Prior Publication Data
US 2021/0207115 A1 Jul. 8, 2021

(30) Foreign Application Priority Data
Dec. 11, 2017 (CN) .......................... 201711310506.2

(51) Int. Cl.
| | | |
|---|---|---|
| C07K 14/745 | (2006.01) | |
| C12N 9/64 | (2006.01) | |
| A61P 7/04 | (2006.01) | |
| A61K 48/00 | (2006.01) | |
| C12N 15/85 | (2006.01) | |
| A61K 38/00 | (2006.01) | |

(52) U.S. Cl.
CPC .......... *C12N 9/6443* (2013.01); *A61K 48/005* (2013.01); *A61P 7/04* (2018.01); *C12N 15/85* (2013.01); *C12Y 304/21027* (2013.01); *A61K 38/00* (2013.01); *C12N 2800/107* (2013.01)

(58) Field of Classification Search
None
See application file for complete search history.

(56) References Cited

FOREIGN PATENT DOCUMENTS

| | | |
|---|---|---|
| CN | 102559720 | 7/2012 |
| CN | 108220274 | 6/2018 |
| WO | 2016207858 | 12/2016 |

OTHER PUBLICATIONS

Wiewel-Verschueren et al., J Obstet Gynaecol. Oct. 2017;37(7):912-918. doi: 10.1080/01443615.2017.1312303. Epub Jun. 13, 2017. PMID: 28609141.*
Stryer, L., Biochemistry, 4th edition, W. H. Freeman and Company, 1995, pp. 18-23.*
Skolnick et al., Trends Biotechnol. Jan. 2000;18(1):34-9. doi: 10.1016/s0167-7799(99)01398-0. PMID: 10631780.*
Attwood et al., Science. Oct. 20, 2000;290(5491):471-3. doi: 10.1126/science.290.5491.471. PMID: 11183771.*
Tiscia et al., Hum Genome Var. Nov. 9, 2017;4:17043. doi: 10.1038/hgv.2017.43. eCollection 2017. PMID: 29138690.*
Zucker et al., Haematologica. Oct. 2007;92(10):1375-80. doi: 10.3324/haematol.11526. PMID: 18024374.*
"International Search Report (Form PCT/ISA/210) of PCT/CN2018/103201," dated Dec. 6, 2018, with English translation thereof, pp. 1-6.
Sophie Wiewel-Verschueren, et al., "Factor 11 single-nucleotide variants in women with heavy menstrual bleeding," Journal of Obstetrics and Gynaecology, vol. 37, Jun. 2017, pp. 1-8.

\* cited by examiner

*Primary Examiner* — Michael Szperka
(74) *Attorney, Agent, or Firm* — JCIP GLOBAL INC.

(57) ABSTRACT

Methods of preparing and using a highly active blood coagulation factor XI mutant and a gene therapy/editing vector thereof and a recombinant/fusion protein thereof. The nucleotide sequence of the mutant is as shown in SEQ ID NOs: 1-6, and the amino acid sequence is as shown in SEQ ID NO: 7.

5 Claims, 14 Drawing Sheets
Specification includes a Sequence Listing.

```
   1  ATGATTTTCTTATAT CAAGTGGTACATTTC ATTTTATTTACTTCA GTTTCTGGTGAATGT GTGACTCAGTTGTTG
   1  M   I   F   L   Y   Q   V   V   H   F   I   L   F   T   S   V   S   G   E   C   V   T   Q   L   L
  76  AAGGACACCTGCTTT GAAGGAGGGGACATT ACTACGGTCTTCACA CCAAGCGCCAAGTAC TGCCAGGTAGTCTGC
  26  K   D   T   C   F   E   G   G   D   I   T   T   V   F   T   P   S   A   K   Y   C   Q   V   V   C
 151  ACTTACCACCCAAGA TGTTTACTCTTCACT TTCACGGCGGAATCA CCATCTGAGGATCCC ACCCGATGGTTTACT
  51  T   Y   H   P   R   C   L   L   F   T   F   T   A   E   S   P   S   E   D   P   T   R   W   F   T
 226  TGTGTCCTGAAAGAC AGTGTTACAGAAACA CTGCCAAGAGTGAAT AGGACAGCAGCGATT TCTGGGTATTCTTTC
  76  C   V   L   K   D   S   V   T   E   T   L   P   R   V   N   R   T   A   A   I   S   G   Y   S   F
 301  AAGCAATGCTCACAC CAAATACGCTTGC AACAAGGATATCTAT GTGGACCTAGACATG AAGGGCATAAACTAT
 101  K   Q   C   S   H   Q   I   S   A   C   N   K   D   I   Y   V   D   L   D   M   K   G   I   N   Y
 376  AACAGCTCAGTTGCC AAGAGTGCTCAAGAA TGCCAAGAAAGATGC ACGGATGACGTCCAC TGCCACTTTTTCACG
 126  N   S   S   V   A   K   S   A   Q   E   C   Q   E   R   C   T   D   D   V   H   C   H   F   F   T
 451  TACGCCACAAGGCAG TTTCCCAGCCTGGAG CATCGTAACATTTGT CTACTGAAGCACACC CAAACAGGGACACCA
 151  Y   A   T   R   Q   F   P   S   L   E   H   R   N   I   C   L   L   K   H   T   Q   T   G   T   P
 526  ACCAGAATAACGAAG CTCGATAAAGTGGTG TCTGGATTTTCACTG AAATCCTGTGCACTT TCTAATCTGGCTTGT
 176  T   R   I   T   K   L   D   K   V   V   S   G   F   S   L   K   S   C   A   L   S   N   L   A   C
 601  ATTAGGGACATTTTC CCTAATACGGTGTTT GCAGACAGCAACATC GACAGTGTCATGGCT CCCGATGCTTTTGTC
 201  I   R   D   I   F   P   N   T   V   F   A   D   S   N   I   D   S   V   M   A   P   D   A   F   V
 676  TGTGGCCGAATCTGC ACTCATCATCCCGGT TGCTTGTTTTTTACC TTCTTTTCCCAGGAA TGGCCCAAAGAATCT
 226  C   G   R   I   C   T   H   H   P   G   C   L   F   F   T   F   F   S   Q   E   W   P   K   E   S
 751  CAAAGAAATCTTTGT CTCCTTAAACATCT GAGAGTGGATTGCCC AGTACACGCATTAAA AAGACGCAAAGCTCTT
 251  Q   R   N   L   C   L   L   K   T   S   E   S   G   L   P   S   T   R   I   K   K   S   K   A   L
 826  TCTGGTTTCAGTCTA CAAAGCTGCAGGCAC AGCATCCAGTGTTC TGCCATTCTTCATTT TACCATGACACTGAT
 276  S   G   F   S   L   Q   S   C   R   H   S   I   P   V   F   C   H   S   S   F   Y   H   D   T   D
 901  TTCTTGGAGAAGAA CTGGATATTGTTGCT GCAAAAAGTCACGAG GCCTGCCAGAAACTG TGCACCAATGCCGTC
 301  F   L   G   E   E   L   D   I   V   A   A   K   S   H   E   A   C   Q   K   L   C   T   N   A   V
 976  CGCTGCCAGTTTTTT ACCTATACCCCAGCC CAAGCATCCTGCAAC GAAGGGAAGGGCAAG TGTTACTTAAAGCTT
 326  R   C   Q   F   F   T   Y   T   P   A   Q   A   S   C   N   E   G   K   G   K   C   Y   L   K   L
1051  TCTTCAAACGGATCT CCAACTAAAATACTT CACGGGAGAGGAGGC ATCTCTGGATACACA TTAAGGTTGTGTAAA
 351  S   S   N   G   S   P   T   K   I   L   H   G   R   G   G   I   S   G   Y   T   L   R   L   C   K
1126  ATGGATAATGAGTGT ACCACCAAAATCAAG CCCGGATCGTTGGA GGAACTGCGTCTGTT CGTACTGAGTGGCCG
 376  M   D   N   E   C   T   T   K   I   K   P   R   I   V   G   T   A   S   V   R   S   E   W   P
1201  TGGCAGGTGACCCTG CACACAACCTCACCC ACTCAGAGACACCTG TGTGGAGGCTCCATC ATTGGAAACCAGTGG
 401  W   Q   V   T   L   H   T   T   S   P   T   Q   R   H   L   C   G   G   S   I   I   G   N   Q   W
1276  ATATTAACAGCCGCT CACTGTTTCTATGGG GTAGAGTCACCTAAG ATTTTGCGTGTCTAC AGTGGCATTTTAAAT
 426  I   L   T   A   A   H   C   F   Y   G   V   E   S   P   K   I   L   R   V   Y   S   G   I   L   N
1351  CAATCTGAAATAAAA GAGGACACATCTTTC TTTGGGGTTCAAGAA ATAATAATCCATGAT CAGTATAAAATGGCA
 451  Q   S   E   I   K   E   D   T   S   F   F   G   V   Q   E   I   I   I   H   D   Q   Y   K   M   A
1426  GAAAGCGGGTATGAT ATTGCCTTGTTGAAA CTGGAAACCACAGTG AATTACACAGATTCT CAACGACCCATATGC
 476  E   S   G   Y   D   I   A   L   L   K   L   E   T   T   V   N   Y   T   D   S   Q   R   P   I   C
1501  CTGCCTTCCAAAGGA GATAGAAATGTAATA TACACTGATTGCTGG GTGACTGGATGGGGG TACAGAAAACTAAGA
 501  L   P   S   K   G   D   R   N   V   I   Y   T   D   C   W   V   T   G   W   G   Y   R   K   L   R
1576  GACAAAATACAAAAT ACTCTCCAGAAAGCC AAGATACCCTTAGTG ACCAACGAAGAGTGC CAGAAGAGATACAGA
 526  D   K   I   Q   N   T   L   Q   K   A   K   I   P   L   V   T   N   E   E   C   Q   K   R   Y   R
1651  GGACATAAAATAACC CATAAGATGATCTGT GCCGGCTACAGGGAA GGAGGGAAGGACGCT TGCAAGGGAGATTCG
 551  G   H   K   I   T   H   K   M   I   C   A   G   Y   R   E   G   G   K   D   A   C   K   G   D   S
1726  GGAGGCCCTCTGTCC TGCAAACACAATGAG GTCTGGCATCTGGTA GGCATCACGAGCTGG GGCGAAGGCTGTGCT
 576  G   G   P   L   S   C   K   H   N   E   V   W   H   L   V   G   I   T   S   W   G   E   G   C   A
1801  CAAAGGGAGCGGCCA GGTGTTTACACCAAC GTGGTCGAGTACGTG GACTGGATTCTGGAG AAAACTCAAGCAGTG
 601  Q   R   E   R   P   G   V   Y   T   N   V   V   E   Y   V   D   W   I   L   E   K   T   Q   A   V
1876  TGA
 626  *
```

FIG. 1

```
  1  ATGATTTTCTTATAT CAAGTGGTACATTTC ATTTTATTTACTTCA GTTTCTGGTGAATGT GTGACTCAGTTGTTG
  1   M  I  F  L  Y   Q  V  V  H  F   I  L  F  T  S   V  S  G  E  C   V  T  Q  L  L
 76  AAGGACACCTGCTTT GAAGGAGGGGACATT ACTACGGTCTTCACA CCAAGCGCCAAGTAC TGCCAGGTAGTCTGC
 26   K  D  T  C  F   E  G  G  D  I   T  T  V  F  T   P  S  A  K  Y   C  Q  V  V  C
151  ACTTACCACCCAAGA TGTTTACTCTTCACT TTCACGGCGGAATCA CCATCTGAGGATCCC ACCCGATGGTTTACT
 51   T  Y  H  P  R   C  L  L  F  T   F  T  A  E  S   P  S  E  D  P   T  R  W  F  T
226  TGTGTCCTGAAAGAC AGTGTTACAGAAACA CTGCCAAGAGTGAAT AGGACAGCAGCGATT TCTGGGTATTCTTTC
 76   C  V  L  K  D   S  V  T  E  T   L  P  R  V  N   R  T  A  A  I   S  G  Y  S  F
301  AAGCAATGCTCACAC CAAATAAGCGCTTGC AACAAAGACATTTAT GTGGACCTAGACATG AAGGGCATAAACTAT
101   K  Q  C  S  H   Q  I  S  A  C   N  K  D  I  Y   V  D  L  D  M   K  G  I  N  Y
376  AACAGCTCAGTTGCC AAGAGTGCTCAAGAA TGCCAAGAAAGATGC ACGGATGACGTCCAC TGCCACTTTTCACG
126   N  S  S  V  A   K  S  A  Q  E   C  Q  E  R  C   T  D  D  V  H   C  H  F  F  T
451  TACGCCACAAGGCAG TTTCCCAGCCTGGAG CATCGTAACATTTGT CTACTGAAGCACACC CAAACAGGGACACCA
151   Y  A  T  R  Q   F  P  S  L  E   H  R  N  I  C   L  L  K  H  T   Q  T  G  T  P
526  ACCAGAATAACGAAG CTCGATAAAGTGGTG TCTGGATTTTCACTG AAATCCTGTGCACTT TCTAATCTGGCTTGT
176   T  R  I  T  K   L  D  K  V  V   S  G  F  S  L   K  S  C  A  L   S  N  L  A  C
601  ATTAGGGACATTTTC CCTAATACGGTGTTT GCAGACAGCAACATC GACAGTGTCATGGCT CCCGATGCTTTTGTC
201   I  R  D  I  F   P  N  T  V  F   A  D  S  N  I   D  S  V  M  A   P  D  A  F  V
676  TGTGGCCGAATCTGC ACTCATCATCCCGGT GCTTGTTTTTACC TTCTTTTCCCAGGAA TGGCCCAAAGAATCT
226   C  G  R  I  C   T  H  H  P  G   C  L  F  F  T   F  S  Q  E   W  P  K  E  S
751  CAAAGAAATCTTTGT CTCCTTAAAACATCT GAGAGTGGATTGCCC AGTACACGCATTAAA AAGAGCAAAGCTCTT
251   Q  R  N  L  C   L  L  K  T  S   E  S  G  L  P   S  T  R  I  K   K  S  K  A  L
826  TCTGGTTTCAGTCTA CAAAGCTGCAGGCAC AGCATCCAGTGTTC TGCCATTCTTCATTT TACCATGACACTGAT
276   S  G  F  S  L   Q  S  C  R  H   S  I  P  V  F   C  H  S  S  F   Y  H  D  T  D
901  TTCTTGGGAGAAGAA CTGGATATTGTTGCT GCAAAAAGTCACGAG GCCTGCCAGAAACTG TGCACCAATGCCGTC
301   F  L  G  E  E   L  D  I  V  A   A  K  S  H  E   A  C  Q  K  L   C  T  N  A  V
976  CGCTGCCAGTTTTTT ACCTATACCCCAGCC CAAGCATCCTGCAAC GAAGGGAAGGGCAAG TGTTACTTAAAGCTT
326   R  C  Q  F  F   T  Y  T  P  A   Q  A  S  C  N   E  G  K  G  K   C  Y  L  K  L
1051 TCTTCAAACGGATCT CCAACTAAAATACTT CACGGGAGAGGAGGC ATCTCTGGATACACA TTAAGGTTGTGTAAA
351   S  S  N  G  S   P  T  K  I  L   H  G  R  G  G   I  S  G  Y  T   L  R  L  C  K
1126 ATGGATAATGAGTGT ACCACCAAAATCAAG CCCAGGATCGTTGGA GGAACTGCGTCTGTT CGTAACGAGTGGCCG
376   M  D  N  E  C   T  T  K  I  K   P  R  I  V  G   G  T  A  S  V   R  N  E  W  P
1201 TGGCAGGTGACCCTG CACACAACCTCACCC ACTCAGAGACACCTG TGTGGAGGCTCCATC ATTGGAAACCAGTGG
401   W  Q  V  T  L   H  T  T  S  P   T  Q  R  H  L   C  G  G  S  I   I  G  N  Q  W
1276 ATATTAACAGCCGCT CACTGTTTCTATGGG GTAGAGTCACCTAAG ATTTTGCGTGTCTAC AGTGGCATTTTAAAT
426   I  L  T  A  A   H  C  F  Y  G   V  E  S  P  K   I  L  R  V  Y   S  G  I  L  N
1351 CAATCTGAAATAAAA GAGGACACATCTTTC TTTGGGGTTCAAGAA ATAATAATCCATGAT CAGTATAAAATGGCA
451   Q  S  E  I  K   E  D  T  S  F   F  G  V  Q  E   I  I  I  H  D   Q  Y  K  M  A
1426 GAAAGCGGGTATGAT ATTGCCTTGTTGAAA CTGAAACACAGTGA AATTACACAGATTCT CAACGACCCATATGC
476   E  S  G  Y  D   I  A  L  L  K   L  E  T  T  V   N  Y  T  D  S   Q  R  P  I  C
1501 CTGCCTTCCAAAGGA GATAGAAATGTAATA TACACTGATTGCTGG GTGACTGGATGGGGG TACAGAAAACTAAGA
501   L  P  S  K  G   D  R  N  V  I   Y  T  D  C  W   V  T  G  W  G   Y  R  K  L  R
1576 GACAAAATACAAAAT ACTCTCCAGAAAGCC AAGATACCCTTAGTG ACCAACGAAGATGC AGAAGAGATACGA
526   D  K  I  Q  N   T  L  Q  K  A   K  I  P  L  V   T  N  E  E  C   Q  K  R  Y  R
1651 GGACATAAAATAACC CATAAGATGATCTGT GCCGGCTACAGGGAA GGAGGGAAGGACGCT TGCAAGGGAGATTCG
551   G  H  K  I  T   H  K  M  I  C   A  G  Y  R  E   G  G  K  D  A   C  K  G  D  S
1726 GGAGGCCCTCTGTCC TGCAAACACAATGAG GTCTGGCATCTGGTA GGCATCACGAGCTGG GGCGAAGGCTGTGCT
576   G  G  P  L  S   C  K  H  N  E   V  W  H  L  V   G  I  T  S  W   G  E  G  C  A
1801 CAAAGGGAGCGGCCA GGTGTTTACACCAAC GTGGTCGAGTACGTG GACTGGATTCTGGAG AAAACTCAAGCAGTG
601   Q  R  E  R  P   G  V  Y  T  N   V  V  E  Y  V   D  W  I  L  E   K  T  Q  A  V
1876 TGA
626   *
```

FIG. 2

```
   1 ATGATTTTCTTATAT CAAGTGGTACATTTC ATTTTATTTACTTCA GTTTCTGGTGAATGT GTGACTCAGTTGTTG
   1 M  I  F  L  Y    Q  V  V  H  F    I  L  F  T  S    V  S  G  E  C    V  T  Q  L  L
  76 AAGGACACCTGCTTT GAAGGAGGGGACATT ACTACGGTCTTCACA CCAAGCGCCAAGTAC TGCCAGGTAGTCTGC
  26 K  D  T  C  F    E  G  G  D  I    T  T  V  F  T    P  S  A  K  Y    C  Q  V  V  C
 151 ACTTACCACCCAAGA TGTTTACTCTTCACT TTCACGGCGGAATCA CCATCTGAGGATCCC ACCCGATGGTTTACT
  51 T  Y  H  P  R    C  L  L  F  T    F  T  A  E  S    P  S  E  D  P    T  R  W  F  T
 226 TGTGTCCTGAAAGAC AGTGTTACAGAAACA CTGCCAAGAGTGAAT AGGACAGCAGCGATT TCTGGGTATTCTTTC
  76 C  V  L  K  D    S  V  T  E  T    L  P  R  V  N    R  T  A  A  I    S  G  Y  S  F
 301 AAGCAATGCTCACAC CAAATAAGCGCTTAA ACAAGACATTTAT GTGGACCTAGACATG AAGGGCATAAACTAT
 101 K  Q  C  S  H    Q  I  S  A  C    N  K  D  I  Y    V  D  L  D  M    K  G  I  N  Y
 376 AACAGCTCAGTTGCC AAGAGTGCTCAAGAA TGCCAAGAAAGATGC ACGGATGACGTCCAC TGCCACTTTTTCACG
 126 N  S  S  V  A    K  S  A  Q  E    C  Q  E  R  C    T  D  D  V  H    C  H  F  F  T
 451 TACGCCACAAGGCAG TTTCCCAGCCTGGAG CATCGTAACATTTGT CTACTGAAGCACACC CAAACAGGGACACCA
 151 Y  A  T  R  Q    F  P  S  L  E    H  R  N  I  C    L  L  K  H  T    Q  T  G  T  P
 526 ACCAGAATAACGAAG CTCGATAAAGTGGTG TCTGGATTTTCACTG AAATCCTGTGCACTT TCTAATCTGGCTTGT
 176 T  R  I  T  K    L  D  K  V  V    S  G  F  S  L    K  S  C  A  L    S  N  L  A  C
 601 ATTAGGGACATTTTC CCTAATACGGTGTTT GCAGACAGCAACATC GACAGTGTCATGGCT CCCGATGCTTTTGTC
 201 I  R  D  I  F    P  N  T  V  F    A  D  S  N  I    D  S  V  M  A    P  D  A  F  V
 676 TGTGGCCGAATCTGC ACTCATCATCCCGGT TGCTTGTTTTTTACC TTCTTTCCCAGGAA TGGCCAAAGAATCT
 226 C  G  R  I  C    T  H  H  P  G    C  L  F  F  T    F  F  P  Q  E    W  P  K  E  S
 751 CAAAGAAATCTTTGT CTCCTTAAAACATCT GAGAGTGGATTGCCC AGTACACGCATTAAA AAGAGCAAAGCTCTT
 251 Q  R  N  L  C    L  L  K  T  S    E  S  G  L  P    S  T  R  I  K    K  S  K  A  L
 826 TCTGGTTTCAGTCTA CAAAGCTGCAGGCAC AGCATCCCAGTGTTC TGCCATTCTTCATTT TACCATGACACTGAT
 276 S  G  F  S  L    Q  S  C  R  H    S  I  P  V  F    C  H  S  S  F    Y  H  D  T  D
 901 TTCTTGGGAGAAGAA CTGGATATTGTTGCT GCAAAAAGTCACGAG GCCTGCCAGAAACTG TGCACCAATGCCGTC
 301 F  L  G  E  E    L  D  I  V  A    A  K  S  H  E    A  C  Q  K  L    C  T  N  A  V
 976 CGCTGCCAGTTTTTT ACCTATACCCCAGCC AAGCATCCTGCAAC GAAGGGAAGGCAAG TGTTACTTAAAGCTT
 326 R  C  Q  F  F    T  Y  T  P  A    Q  A  S  C  N    E  G  K  G  K    C  Y  L  K  L
1051 TCTTCAAACGGATCT CCAACTAAAATACTT CACGGAGGAGGC ATCTCTGGATACA TTAAGGTTGTGTAAA
 351 S  S  N  G  S    P  T  K  I  L    H  G  R  G  G    I  S  G  Y  T    L  R  L  C  K
1126 ATGGATAATGAGTGT ACCACCAAAATCAAG CCCAGGATCGTTGGA GGAACTGCCGTCTGTT CGTCTGAGTGGCCG
 376 M  D  N  E  C    T  T  K  I  K    P  R  I  V  G    T  A  S  V    R  [S]  E  W  P
1201 TGGCAGGTGACCCTG CACACAACCTCACCC ACTCAGAGACACCTG TGTGGAGGCTCCATC ATTGGAAACCAGTGG
 401 W  Q  V  T  L    H  T  T  S  P    T  Q  R  H  L    C  G  G  S  I    I  G  N  Q  W
1276 ATATTAACAGCCGCT CACTGTTTCTATGGG GTAGAGTCACCTAAG ATTTTGCGTGTCTAC AGTGGCATTTTAAAT
 426 I  L  T  A  A    H  C  F  Y  G    V  E  S  P  K    I  L  R  V  Y    S  G  I  L  N
1351 CAATCTGAAATAAAA GAGGACACATCTTTC TTTGGGGTTCAAGAA ATAATAATCCATGAT CAGTATAAAATGGCA
 451 Q  S  E  I  K    E  D  T  S  F    F  G  V  Q  E    I  I  I  H  D    Q  Y  K  M  A
1426 GAAAGCGGGTATGAT ATTGCCTTGTTGAAA CTGGAAACCACAGTG AATTACACAGATTCT CAACGACCCATATGC
 476 E  S  G  Y  D    I  A  L  L  K    L  E  T  T  V    N  Y  T  D  S    Q  R  P  I  C
1501 CTGCCTTCCAAAGGA GATAGAAATGTAATA TACACTGATTGCTGG GTGACTGGATGGGGG TACAGAAAACTAAGA
 501 L  P  S  K  G    D  R  N  V  I    Y  T  D  C  W    V  T  G  W  G    Y  R  K  L  R
1576 GACAAAATACAAAAT ACTCTCCAGAAAGCC AAGATACCCTTAGTG ACCAACGAAGAGTGC CAGAAGAGATACAGA
 526 D  K  I  Q  N    T  L  Q  K  A    K  I  P  L  V    T  N  E  E  C    Q  K  R  Y  R
1651 GGACATAAAATAACC CATAAGATGATCTGT GCCGGCTACAGGGAA GGAGGGAAGGACGCT TGCAAGGGAGATTCG
 551 G  H  K  I  T    H  K  M  I  C    A  G  Y  R  E    G  G  K  D  A    C  K  G  D  S
1726 GGAGGCCCTCTGTCC TGCAAACACAATGAG GTCTGGCATCTGGTA GGCATCACGAGCTGG GGCGAAGGCTGTGCT
 576 G  G  P  L  S    C  K  H  N  E    V  W  H  L  V    G  I  T  S  W    G  E  G  C  A
1801 CAAAGGGAGCGGCCA GGTGTTTACACCAAC GTGGTCGAGTACGTG GACTGGATTCTGGAG AAAACTCAAGCAGTG
 601 Q  R  E  R  P    G  V  Y  T  N    V  V  E  Y  V    D  W  I  L  E    K  T  Q  A  V
1876 TGA
 626 *
```

FIG. 3

```
   1 ATGATTTTCTTATAT CAAGTGGTACATTTC ATTTTATTTACTTCA GTTTCTGGTGAATGT GTGACTCAGTTGTTG
   1  M  I  F  L  Y   Q  V  V  H  F   I  L  F  T  S   V  S  G  E  C   V  T  Q  L  L
  76 AAGGACACCTGCTTT GAAGGAGGGGACATT ACTACGGTCTTCACA CCAAGCGCCAAGTAC TGCCAGGTAGTCTGC
  26  K  D  T  C  F   E  G  G  D  I   T  T  V  F  T   P  S  A  K  Y   C  Q  V  V  C
 151 ACTTACCACCCAAGA TGTTTACTCTTCACT TTCACGGCGGAATCA CCATCTGAGGATCCC ACCCGATGGTTTACT
  51  T  Y  H  P  R   C  L  L  F  T   F  T  A  E  S   P  S  E  D  P   T  R  W  F  T
 226 TGTGTCCTGAAAGAC AGTGTTACAGAAACA CTGCCAAGAGTGAAT AGGACAGCAGCAGCATT TCTGGGTATTCTTTC
  76  C  V  L  K  D   S  V  T  E  T   L  P  R  V  N   R  T  A  A  I   S  G  Y  S  F
 301 AAGCAATGCTCACAC CAAATAAGCGCTTGC AACAAAGACATTTAT GTGGACCTAGACATG AAGGGCATAAACTAT
 101  K  Q  C  S  H   Q  I  S  A  C   N  K  D  I  Y   V  D  L  D  M   K  G  I  N  Y
 376 AACAGCTCAGTTGCC AAGAGTGCTCAAGAA TGCCAAGAAAGATGC ACGGATGACGTCCAC TGCCACTTTTTCACG
 126  N  S  S  V  A   K  S  A  Q  E   C  Q  E  R  C   T  D  D  V  H   C  H  F  F  T
 451 TACGCCACAAGGCAG TTTCCCAGCCTGGAG CATCGTAACATTTGT CTACTGAAGCACACC CAAACAGGGACACCA
 151  Y  A  T  R  Q   F  P  S  L  E   H  R  N  I  C   L  L  K  H  T   Q  T  G  T  P
 526 ACCAGAATAACGAAG CTCGATAAAGTGGTG TCTGGATTTTCACTG AAATCCTGTGCACTT TCTAATCTGGCTTGT
 176  T  R  I  T  K   L  D  K  V  V   S  G  F  S  L   K  S  C  A  L   S  N  L  A  C
 601 ATTAGGGACATTTTC CCTAATACGGTGTTT GCAGACAGCAACATC GACAGTGTCATGGCT CCCGATGCTTTTGTC
 201  I  R  D  I  F   P  N  T  V  F   A  D  S  N  I   D  S  V  M  A   P  D  A  F  V
 676 TGTGGCCGAATCTGC ACTCATCATCCCGGT GCTTGTTTTTTACC TTCTTTTCCCAGGAA TGGCCCAAAGAATCT
 226  C  G  R  I  C   T  H  H  P  G   C  L  F  F  T   F  F  S  Q  E   W  P  K  E  S
 751 CAAAGAAATCTTTGT CTCCTTAAAACATCT GAGAGTGGATTGCCC AGTACACGCATTAAA AAGAGCAAAGCTCTT
 251  Q  R  N  L  C   L  L  K  T  S   E  S  G  L  P   S  T  R  I  K   K  S  K  A  L
 826 TCTGGTTTCAGTCTA CAAAGCTGCAGGCAC AGCATCCCAGTGTTC TGCCATTCTTCATTT TACCATGACACTGAT
 276  S  G  F  S  L   Q  S  C  R  H   S  I  P  V  F   C  H  S  S  F   Y  H  D  T  D
 901 TTCTTGGGAGAAGAA CTGGATATTGTTGCT GCAAAAAGTCACGAG GCCTGCCAGAAACTG TGCACCAATGCCGTC
 301  F  L  G  E  E   L  D  I  V  A   A  K  S  H  E   A  C  Q  K  L   C  T  N  A  V
 976 CGCTGCCAGTTTTT ACCTATACCCCAGCC CAAGCATCCTGCAAC GAAGGGAAGGGCAAG TGTTACTTAAAGCTT
 326  R  C  Q  F  F   T  Y  T  P  A   Q  A  S  C  N   E  G  K  G  K   C  Y  L  K  L
1051 TCTTCAAACGGATCT CCAACTAAAATACTT CACGGGAGAGGAGGC ATCTCTGGATACACA TTAAGGTTGTGTAAA
 351  S  S  N  G  S   P  T  K  I  L   H  G  R  G  G   I  S  G  Y  T   L  R  L  C  K
1126 ATGGATAATGAGTGT ACCACCAAAATCAAG CCCAGGATCGTTGGA GGAACTGCGTCTGTT CGTTCCGAGTGGCCG
 376  M  D  N  E  C   T  T  K  I  K   P  R  I  V  G   G  T  A  S  V   R  S  E  W  P
1201 TGGCAGGTGACCCTG CACACAACCTCACCC ACTCAGAGACACTG TGTGGAGGCTCCATC ATTGGAAACCAGTGG
 401  W  Q  V  T  L   H  T  T  S  P   T  Q  R  H  L   C  G  G  S  I   I  G  N  Q  W
1276 ATATTAACAGCCGCT CACTGTTTCTATGGG GTAGAGTCACCTAAG ATTTTGCGTGTCTAC AGTGGCATTTTAAAT
 426  I  L  T  A  A   H  C  F  Y  G   V  E  S  P  K   I  L  R  V  Y   S  G  I  L  N
1351 CAATCTGAAATAAAA GAGGACACATCTTTC TTTGGGGTTCAAGAA ATAATAATCCATGAT CAGTATAAAATGGCA
 451  Q  S  E  I  K   E  D  T  S  F   F  G  V  Q  E   I  I  I  H  D   Q  Y  K  M  A
1426 GAAAGCGGGTATGAT ATTGCCTTGTTGAAA CTGGAAACCACAGTG AATTACACAGATTCT CAACGACCCATATGC
 476  E  S  G  Y  D   I  A  L  L  K   L  E  T  T  V   N  Y  T  D  S   Q  R  P  I  C
1501 CTGCCTTCCAAAGGA GATAGAAATGTAATA TACACTGATTGCTGG GTGACTGGATGGGGG TACAGAAAACTAAGA
 501  L  P  S  K  G   D  R  N  V  I   Y  T  D  C  W   V  T  G  W  G   Y  R  K  L  R
1576 GACAAAATACAAAAT ACTCTCCAGAAAGCC AAGATACCCTTAGTG ACCAACGAAGAGTGC CAGAAGAGATACAGA
 526  D  K  I  Q  N   T  L  Q  K  A   K  I  P  L  V   T  N  E  E  C   Q  K  R  Y  R
1651 GGACATAAAATAACC CATAAGATGATCTGT GCCGGCTACAGGGAA GGAGGGAAGGACGCT TGCAAGGGAGATTCG
 551  G  H  K  I  T   H  K  M  I  C   A  G  Y  R  E   G  G  K  D  A   C  K  G  D  S
1726 GGAGGCCCTCTGTCC TGCAAACACAATGAG GTCTGGCATCTGGTA GGCATCACGAGCTGG GGCGAAGGCTGTGCT
 576  G  G  P  L  S   C  K  H  N  E   V  W  H  L  V   G  I  T  S  W   G  E  G  C  A
1801 CAAAGGGAGCGGCCA GGTGTTTACACCAAC GTGGTCGAGTACGTG GACTGGATTCTGGAG AAAACTCAAGCAGTG
 601  Q  R  E  R  P   G  V  Y  T  N   V  V  E  Y  V   D  W  I  L  E   K  T  Q  A  V
1876 TGA
 626  *
```

FIG. 4

```
   1 ATGATTTTCTTATAT CAAGTGGTACATTTC ATTTTATTTACTTCA GTTTCTGGTGAATGT GTGACTCAGTTGTTG
   1  M  I  F  L  Y   Q  V  V  H  F   I  L  F  T  S   V  S  G  E  C   V  T  Q  L  L
  76 AAGGACACCTGCTTT GAAGGAGGGGACATT ACTACGGTCTTCACA CCAAGCGCCAAGTAC TGCCAGGTAGTCTGC
  26  K  D  T  C  F   E  G  G  D  I   T  T  V  F  T   P  S  A  K  Y   C  Q  V  V  C
 151 ACTTACCACCCAAGA TGTTTACTCTTCACT TTCACGGCGGAATCA CCATCTGAGGATCCC ACCCGATGGTTTACT
  51  T  Y  H  P  R   C  L  L  F  T   F  T  A  E  S   P  S  E  D  P   T  R  W  F  T
 226 TGTGTCCTGAAAGAC AGTGTTACAGAAACA CTGCCAAGAGTGAAT AGGACAGCAGCGATT TCTGGGTATTCTTTC
  76  C  V  L  K  D   S  V  T  E  T   L  P  R  V  N   R  T  A  A  I   S  G  Y  S  F
 301 AAGCAATGCTCACAC CAAATAAGCGCTTGC AACAAAGACATTTAT GTGGACCTAGACATG AAGGGCATAAACTAT
 101  K  Q  C  S  H   Q  I  S  A  C   N  K  D  I  Y   V  D  L  D  M   K  G  I  N  Y
 376 AACAGCTCAGTTGCC AAGAGTGCTCAAGAA TGCCAAGAAAGATGC ACGGATGACGTCCAC TGCCACTTTTTCACG
 126  N  S  S  V  A   K  S  A  Q  E   C  Q  E  R  C   T  D  D  V  H   C  H  F  F  T
 451 TACGCCACAAGGCAG TTTCCCAGCCTGGAG CATCGTAACATTTGT CTACTGAAGCACACC CAAACGGGACACCA
 151  Y  A  T  R  Q   F  P  S  L  E   H  R  N  I  C   L  L  K  H  T   Q  T  G  T  P
 526 ACCAGAATAACGAAG CTCGATAAAGTGGTG TCTGGATTTTCACTG AAATCCTGTGCACTT TCTAATCTGGCTTGT
 176  T  R  I  T  K   L  D  K  V  V   S  G  F  S  L   K  S  C  A  L   S  N  L  A  C
 601 ATTAGGGACATTTTC CCTAATACGGTGTTT GCAGACAGCAACATC GACAGTGTCATGGCT CCCGATGCTTTTGTC
 201  I  R  D  I  F   P  N  T  V  F   A  D  S  N  I   D  S  V  M  A   P  D  A  F  V
 676 TGTGGCCGAATCTGC ACTCATCATCCCGGT TGCTTGTTTTTTACC TTCTTTCCCAGGAA TGGCCCAAAGAATCT
 226  C  G  R  I  C   T  H  H  P  G   C  L  F  F  T   F  F  S  Q  E   W  P  K  E  S
 751 CAAAGAAATCTTTGT CTCCTTAAAACATCT GAGAGTGGATTGCCC AGTACACGCATTAAA AAGAGCAAAGCTCTT
 251  Q  R  N  L  C   L  L  K  T  S   E  S  G  L  P   S  T  R  I  K   K  S  K  A  L
 826 TCTGGTTTCAGTCTA CAAAGCTGCAGGCAC AGCATCCCAGTGTTC TGCCATTCTTCATTT TACCATGACACTGAT
 276  S  G  F  S  L   Q  S  C  R  H   S  I  P  V  F   C  H  S  S  F   Y  H  D  T  D
 901 TTCTTGGGAGAAGAA CTGGATATTGTTGCT GCAAAAAGTCACGAG GCCTGCCAGAAACTG TGCACCAATGCCGTC
 301  F  L  G  E  E   L  D  I  V  A   A  K  S  H  E   A  C  Q  K  L   C  T  N  A  V
 976 CGCTGCCAGTTTTTT ACCTATACCCCAGCC CAAGCATCCTGCAAC GAAGGGAAGGGCAAG TGTTACTTAAAGCTT
 326  R  C  Q  F  F   T  Y  T  P  A   Q  A  S  C  N   E  G  K  G  K   C  Y  L  K  L
1051 TCTTCAAACGGATCT CCAACTAAAATACTT CACGGGAGAGGAGGC ATCTCTGGATACACA TTAAGGTTGTGTAAA
 351  S  S  N  G  S   P  T  K  I  L   H  G  R  G  G   I  S  G  Y  T   L  R  L  C  K
1126 ATGGATAATGAGTGT ACCACCAAAATCAAA CCCAGATGCGTCGTT GGAAGTGCCTGGCCG
 376  M  D  N  E  C   T  T  K  I  K   P  R  I  V  G   T  A  S  V   R  S  E  W  P
1201 TGGCAGGTGACCCTG CACACAACCTCACCC ACTCAGAGACACCTG TGTGGAGGCTCCATC ATTGGAAACCAGTGG
 401  W  Q  V  T  L   H  T  T  S  P   T  Q  R  H  L   C  G  G  S  I   I  G  N  Q  W
1276 ATATTAACAGCCGCT CACTGTTTCTATGGG GTAGAGTCACCTAAG ATTTTGCGTGTCTAC AGTGGCATTTTAAAT
 426  I  L  T  A  A   H  C  F  Y  G   V  E  S  P  K   I  L  R  V  Y   S  G  I  L  N
1351 CAATCTGAAATAAAA GAGGACACATCTTTC TTTGGGGTTCAAGAA ATAATAATCCATGAT CAGTATAAAATGGCA
 451  Q  S  E  I  K   E  D  T  S  F   F  G  V  Q  E   I  I  I  H  D   Q  Y  K  M  A
1426 GAAAGCGGTATGAT ATTGCCTTGTTGAAA CTGGAAACCACAGTG AATTACACAGATTCT CAACGACCCATATGC
 476  E  S  G  Y  D   I  A  L  L  K   L  E  T  T  V   N  Y  T  D  S   Q  R  P  I  C
1501 CTGCCTTCCAAGGA GATAGAAATGTAATA TACACTGATTGCTGG GTGACTGGATGGGGG TACAGAAAACTAAGA
 501  L  P  S  K  G   D  R  N  V  I   Y  T  D  C  W   V  T  G  W  G   Y  R  K  L  R
1576 GACAAAATACAAAAT ACTCTCCAGAAAGCC AAGATACCCTTAGTG ACCAACGAAGAGTGC CAGAAGAGATACAGA
 526  D  K  I  Q  N   T  L  Q  K  A   K  I  P  L  V   T  N  E  E  C   Q  K  R  Y  R
1651 GGACATAAAATAACC CATAAGATGATCTGT GCCGGCTACAGGGAA GGAGGGAAGGACGCT TGCAAGGAGATTCG
 551  G  H  K  I  T   H  K  M  I  C   A  G  Y  R  E   G  G  K  D  A   C  K  G  D  S
1726 GGAGGCCCTCTGTCC TGCAAACACAATGAG GTCGGCATCTGGTA GGCATCACGAGCTGG GGCGAAGGCTGTGCT
 576  G  G  P  L  S   C  K  H  N  E   V  W  H  L  V   G  I  T  S  W   G  E  G  C  A
1801 CAAAGGGAGCGGCCA GGTGTTTACACCAAC GTGGTCGAGTACGTG GACTGGATTCTGGAG AAAACTCAAGCAGTG
 601  Q  R  E  R  P   G  V  Y  T  N   V  V  E  Y  V   D  W  I  L  E   K  T  Q  A  V
1876 TGA
 626  *
```

FIG. 5

```
   1 ATGATTTTCTTATAT CAAGTGGTACATTTC ATTTTATTTACTTCA GTTTCTGGTGAATGT GTGACTCAGTTGTTG
   1  M  I  F  L  Y   Q  V  V  H  F   I  L  F  T  S   V  S  G  E  C   V  T  Q  L  L
  76 AAGGACACCTGCTTT GAAGGAGGGGACATT ACTACGGTCTTCACA CCAAGCGCCAAGTAC TGCCAGGTAGTCTGC
  26  K  D  T  C  F   E  G  G  D  I   T  T  V  F  T   P  S  A  K  Y   C  Q  V  V  C
 151 ACTTACCACCCAAGA TGTTTACTCTTCACT TTCACGGCGGAATCA CCATCTGAGGATCCC ACCCGATGGTTTACT
  51  T  Y  H  P  R   C  L  L  F  T   F  T  A  E  S   P  S  E  D  P   T  R  W  F  T
 226 TGTGTCCTGAAAGAC AGTGTTACAGAAACA CTGCCAAGAGTGAAT AGGACAGCAGCGATT TCTGGGTATTCTTTC
  76  C  V  L  K  D   S  V  T  E  T   L  P  R  V  N   R  T  A  A  I   S  G  Y  S  F
 301 AAGCAATGCTCACAC CAAATAAGCGCTTGC AACAAAGACATTTAT GTGGACCTAGACATG AAGGGCATAAACTAT
 101  K  Q  C  S  H   Q  I  S  A  C   N  K  D  I  Y   V  D  L  D  M   K  G  I  N  Y
 376 AACAGCTCAGTTGCC AAGAGTGCTCAAGAA TGCCAAGAAAGATGC ACGGATGACGTCCAC TGCCACTTTTTCACG
 126  N  S  S  V  A   K  S  A  Q  E   C  Q  E  R  C   T  D  D  V  H   C  H  F  F  T
 451 TACGCCACAAGGCAG TTTCCCAGCCTGGAG CATCGTAACATTTGT CTACTGAAGCACACC CAAACAGGGACACCA
 151  Y  A  T  R  Q   F  P  S  L  E   H  R  N  I  C   L  L  K  H  T   Q  T  G  T  P
 526 ACCAGAATAACGAAG CTCGATAAAGTGGTG TCTGGATTTTCACTG AAATCCTGTGCACTT TCTAATCTGGCTTGT
 176  T  R  I  T  K   L  D  K  V  V   S  G  F  S  L   K  S  C  A  L   S  N  L  A  C
 601 ATTAGGGACATTTTC CCTAATACGGTGTTT GCAGACAGCAACATC GACAGTGTCATGGCT CCCGATGCTTTTGTC
 201  I  R  D  I  F   P  N  T  V  F   A  D  S  N  I   D  S  V  M  A   P  D  A  F  V
 676 TGTGGCCGAATCTGC ACTCATCATCCCGGT TGCTTGTTTTTTACC TTCTTTCCCAGGAA TGGCCCAAAGAATCT
 226  C  G  R  I  C   T  H  H  P  G   C  L  F  F  T   F  F  S  Q  E   W  P  K  E  S
 751 CAAAGAAATCTTTGT CTCCTTAAACATCT GAGAGTGGATTGCCC AGTACACGCATTAAA AAGAGCAAGCTCTT
 251  Q  R  N  L  C   L  L  K  T  S   E  S  G  L  P   S  T  R  I  K   K  S  K  A  L
 826 TCTGGTTTCAGTCTA CAAAGCTGCAGGCAC AGCATCCCAGTGTTC TGCCATTCTTCATTT TACCATGACACTGAT
 276  S  G  F  S  L   Q  S  C  R  H   S  I  P  V  F   C  H  S  S  F   Y  H  D  T  D
 901 TTCTTGGGAGAAGAA CTGGATATTGTTGCT GCAAAAAGTCACGAG GCCTGCCAGAAACTG TGCACCAATGCCGTC
 301  F  L  G  E  E   L  D  I  V  A   A  K  S  H  E   A  C  Q  K  L   C  T  N  A  V
 976 CGCTGCCAGTTTTTT ACCTATACCCCAGCC CAAGCATCCTGCAAC GAAGGGAAGGGCAAG TGTTACTTAAAGCTT
 326  R  C  Q  F  F   T  Y  T  P  A   Q  A  S  C  N   E  G  K  G  K   C  Y  L  K  L
1051 TCTTCAAACGGATCT CCAACTAAAATACTT CACGGAGAGGAGGC ATCTGGATACACA TTAAGGTTGTGTAAA
 351  S  S  N  G  S   P  T  K  I  L   H  G  R  G  G   I  S  G  Y  T   L  R  L  C  K
1126 ATGGATAATGAGTGT ACCACCAAAATCAAG CCCAGGATCGTTGGA GGAACTGCGTCTGTT CGT[CG]AGTGGCCG
 376  M  D  N  E  C   T  T  I  K  P   R  I  V  G   G  T  A  S  V   R [S] E  W  P
1201 TGGCAGGTGACCCTG CACACAACCTCACCC ACTGTGAGACACCTG TGTGGAGGCTCCATC ATTGGAAACCAGTGG
 401  W  Q  V  T  L   H  T  T  S  P   T  Q  R  H  L   C  G  G  S  I   I  G  N  Q  W
1276 ATATTAACAGCCGCT CACTGTTTCTATGGG GTAGAGTCACCTAAG ATTTTGCGTGTCTAC AGTGGCATTTTAAAT
 426  I  L  T  A  A   H  C  F  Y  G   V  E  S  P  K   I  L  R  V  Y   S  G  I  L  N
1351 CAATCTGAAATAAAA GAGGACACATCTTTC TTTGGGGTTCAAGAA ATAATAATCCATGAT CAGTATAAAATGGCA
 451  Q  S  E  I  K   E  D  T  S  F   F  G  V  Q  E   I  I  I  H  D   Q  Y  K  M  A
1426 GAAAGCGGGTATGAT ATTGCCTTGTTGAAA CTGGAAACCACAGTG AATTACACAGATTCT CAACGACCCATATGC
 476  E  S  G  Y  D   I  A  L  L  K   L  E  T  T  V   N  Y  T  D  S   Q  R  P  I  C
1501 CTGCCTTCCAAAGGA GATAGAAATGTAATA TACACTGATTGCTGG GTGACTGGATGGGGG TACAGAAAACTAAGA
 501  L  P  S  K  G   D  R  N  V  I   Y  T  D  C  W   V  T  G  W  G   Y  R  K  L  R
1576 GACAAAATACAAAAT ACTCTCCAGAAAGCC AAGATACCCTTAGTG ACCAACGAAGAGTGC CAGAAGAGATACAGA
 526  D  K  I  Q  N   T  L  Q  K  A   K  I  P  L  V   T  N  E  E  C   Q  K  R  Y  R
1651 GGACATAAAATAACC CATAAGATGATCTGT GCCGGCTACAGGGAA GGAGGGAAGGACGCT TGCAAGGGAGATTCG
 551  G  H  K  I  T   H  K  M  I  C   A  G  Y  R  E   G  G  K  D  A   C  K  G  D  S
1726 GGAGGCCCTCTGTCC TGCAAACACAATGAG GTCTGGCATCTGGTA GGCATCACGAGCTGG GGCGAAGGCTGTGCT
 576  G  G  P  L  S   C  K  H  N  E   V  W  H  L  V   G  I  T  S  W   G  E  G  C  A
1801 CAAAGGGAGCGGCCA GGTGTTTACACCAAC GTGGTCGAGTACGTG GACTGGATTCTGGAG AAAACTCAAGCAGTG
 601  Q  R  E  R  P   G  V  Y  T  N   V  V  E  Y  V   D  W  I  L  E   K  T  Q  A  V
1876 TGA
 626  *
```

FIG. 6

```
  1 MIFLYQVVHF ILFTSVSGEC VTQLLKDTCF EGGDITTVFT PSAKYCQVVC TYHPRCLLFT hFXI
    MIFLYQVVHF ILFTSVSGEC VTQLLKDTCF EGGDITTVFT PSAKYCQVVC TYHPRCLLFT FXI G397S
 61 FTAESPSEDP TRWFTCVLKD SVTETLPRVN RTAAISGYSF KQCSHQISAC NKDIYVDLDM hFXI
    FTAESPSEDP TRWFTCVLKD SVTETLPRVN RTAAISGYSF KQCSHQISAC NKDIYVDLDM FXI G397S
121 KGINYNSSVA KSAQECQERC TDDVHCHFFT YATRQFPSLE HRNICLLKHT QTGTPTRITK hFXI
    KGINYNSSVA KSAQECQERC TDDVHCHFFT YATRQFPSLE HRNICLLKHT QTGTPTRITK FXI G397S
181 LDKVVSGFSL KSCALSNLAC IRDIFPNTVF ADSNIDSVMA PDAFVCGRIC THHPGCLFFT hFXI
    LDKVVSGFSL KSCALSNLAC IRDIFPNTVF ADSNIDSVMA PDAFVCGRIC THHPGCLFFT FXI G397S
241 FFSQEWPKES QRNLCLLKTS ESGLPSTRIK KSKALSGFSL QSCRHSIPVF CHSSFYHDTD hFXI
    FFSQEWPKES QRNLCLLKTS ESGLPSTRIK KSKALSGFSL QSCRHSIPVF CHSSFYHDTD FXI G397S
301 FLGEELDIVA AKSHEACQKL CTNAVRCQFF TYTPAQASCN EGKGKCYLKL SSNGSPTKIL hFXI
    FLGEELDIVA AKSHEACQKL CTNAVRCQFF TYTPAQASCN EGKGKCYLKL SSNGSPTKIL FXI G397S
361 HGRGGISGYT LRLCKMDNEC TTKIKPRIVG GTASVRGEWP WQVTLHTTSP TQRHLCGGSI hFXI
    HGRGGISGYT LRLCKMDNEC TTKIKPRIVG GTASVRSEWP WQVTLHTTSP TQRHLCGGSI FXI G397S
421 IGNQWILTAA HCFYGVESPK ILRVYSGILN QSEIKEDTSF FGVQEIIIHD QYKMAESGYD hFXI
    IGNQWILTAA HCFYGVESPK ILRVYSGILN QSEIKEDTSF FGVQEIIIHD QYKMAESGYD FXI G397S
481 IALLKLETTV NYTDSQRPIC LPSKGDRNVI YTDCWVTGWG YRKLRDKIQN TLQKAKIPLV hFXI
    IALLKLETTV NYTDSQRPIC LPSKGDRNVI YTDCWVTGWG YRKLRDKIQN TLQKAKIPLV FXI G397S
541 TNEECQKRYR GHKITHKMIC AGYREGGKDA CKGDSGGPLS CKHNEVWHLV GITSWGEGCA hFXI
    TNEECQKRYR GHKITHKMIC AGYREGGKDA CKGDSGGPLS CKHNEVWHLV GITSWGEGCA FXI G397S
601 QRERPGVYTN VVEYVDWILE KTQAV*                                      hFXI
    QRERPGVYTN VVEYVDWILE KTQAV*                                      FXI G397S
```

FIG. 7

METHODS FOR PREPARING AND USING HIGHLY ACTIVE BLOOD COAGULATION FACTOR XI MUTANT AND GENE THERAPY/EDITING VECTOR AND RECOMBINANT/FUSION PROTEIN THEREOF

CROSS-REFERENCE TO RELATED APPLICATION

This application is a 371 of international application of PCT application serial no. PCT/CN2018/103201, filed on Aug. 30, 2018, which claims the priority benefit of China application no. 201711310506.2, filed on Dec. 11, 2017. The entirety of each of the above mentioned patent applications is hereby incorporated by reference herein and made a part of this specification.

TECHNICAL FIELD

The present invention belongs to the field for the treatment of hemorrhagic diseases, and in particular, relates to methods for preparing and using a highly active blood coagulation factor XI mutant and a gene therapy/editing vector and a recombinant/fusion protein thereof.

BACKGROUND ART

Hemorrhagic diseases are often caused by blood coagulation factor deficiency or other human coagulation dysfunction. Among them, hemorrhagic diseases caused by blood coagulation factor VIII/IX (FVIII/FIX) deficiency are called hemophilia (type A/B). In severe patients, the blood coagulation factor VIII/IX activity is often lower than 1% of normal level, and spontaneous hemorrhage often occurs leading to muscle hematoma or joint deformity. Currently, the only effective treatment method involves infusing blood coagulation factor VIII/IX preparations (usually blood coagulation factor VIII/IX proteins recombined and expressed in vitro) to increase the blood coagulation factor VIII/IX level in patients, but it requires frequent administration. Gene therapy is a treatment method in clinical trials, which involves introducing the normal blood coagulation factor VIII/IX gene into patients for in vivo expression, so that the level of blood coagulation factor VIII/IX in patients is increased to prevent hemorrhage. Notwithstanding that recombinant or plasma-derived FVIII/FIX can effectively treat hemophilia A and B, about 30% of patients produce antibodies after treatment, rendering the treatment ineffective. Thus, the best choice for the treatment of hemophilia patients with inhibitor production is using bypass blood coagulation active drugs. However, the currently available blood coagulation factor VIIa (FVIIa) for clinical applications is very costly in treatment as it has a short half-life (~2 hours) and requires a large dose (90~100 µg/kg body weight). Therefore, it is imperative to find out how to obtain a novel drug to a bypass coagulation pathway with better therapeutic effect and drug metabolic features for the treatment of hemophilia.

Blood coagulation factor IX is a physiological substrate of blood coagulation factor XI (FXI). The blood coagulation activity of the blood coagulation factor XI is mainly associated with its ability to efficiently cleave and activate blood coagulation factor IX. However, other components in the coagulation reaction may also be catalytically cleaved by the blood coagulation factor XI. Recent studies have shown that blood coagulation factor XI may catalyze the activation of the blood coagulation factor V(FV) and the blood coagulation factor X(FX), thereby bypassing the blood coagulation factor IX to directly activate the common coagulation pathway. Another study has further indicated that blood coagulation factor XI can degrade the tissue factor pathway inhibitor (TFPI), and thus prolong the action time of the exogenous pathway on activating the blood coagulation factor FVII (FVIIa), and indirectly amplify the blood coagulation reaction activated by the exogenous pathway. Nevertheless, the wild-type blood coagulation factor XI has very low efficiency in catalytic cleavage of the bypass coagulation reaction substrate including FX, FV or TFPI, limiting its ability in promoting blood coagulation reaction via an bypass.

SUMMARY OF THE INVENTION

The technical problem to be solved by the present invention is to provide methods of preparing and using a highly active blood coagulation factor XI mutant and a gene therapy/editing vector and a recombinant/fusion protein thereof. The mutant has very high blood coagulation activity, may efficiently activate a blood coagulation reaction via a bypass pathway without dependence on the mechanism of blood coagulation factor IX (FIX)/blood coagulation factor VIII (FVIII), improve the body's overall blood coagulation function, and may be used in the treatment of hemorrhagic diseases. It has good prospects in gene therapy and recombinant protein replacement therapy.

The present invention provides a highly active blood coagulation factor XI mutant, including:

(1) the nucleotide sequence thereof is as shown in SEQ ID NO: 1, the nucleotide at position 1189 is A rather than G; or (2) the nucleotide sequence thereof is as shown in SEQ ID NO: 2, the nucleotide at position 1189 is A rather than G, and the nucleotide at position 1191 is C rather than T; or (3) the nucleotide sequence thereof is as shown in SEQ ID NO: 3, the nucleotide at position 1189 is T rather than G, and the nucleotide at position 1190 is C rather than G; or (4) the nucleotide sequence thereof is as shown in SEQ ID NO: 4, the nucleotide at position 1189 is T rather than G, the nucleotide at position 1190 is C rather than G, and the nucleotide at position 1191 is C rather than T; or (5) the nucleotide sequence thereof is as shown in SEQ ID NO: 5, the nucleotide at position 1189 is T rather than G, the nucleotide at position 1190 is C rather than G, and the nucleotide at position 1191 is A rather than T; or (6) the nucleotide sequence thereof is as shown in SEQ ID NO: 6, the nucleotide at position 1189 is T rather than G, the nucleotide at position 1190 is C rather than G, and the nucleotide at position 1191 is G rather than T; or there is a combination of any other nucleotide mutation at positions 1189, 1190, and 1191.

The present invention also provides a highly active blood coagulation factor XI mutant protein. The amino acid sequence thereof is as shown in SEQ ID NO: 7, the amino acid at position 397 is Ser rather than Gly, or there is any other amino acid change at position 397.

The present invention further provides a nucleic acid encoding the highly active blood coagulation factor XI mutant protein, or a nucleic acid having the same length as and being completely complementary to the encoding nucleic acid.

The present invention still further provides a vector expressing the highly active blood coagulation factor XI mutant protein.

The present invention even still further provides a method for preparing a highly active blood coagulation factor XI mutant protein, including the steps of:

(1) inserting a human coagulation factor IX gene of human wild-type or blood coagulation factor XI Gly397Ser mutant into a vector to obtain a recombinant vector;

(2) transforming a host cell with the above recombinant vector to obtain a cell clone expressing the recombinant blood coagulation factor XI Gly397Ser mutant;

(3) cultivating the above recombinant cell clone in a serum-free medium by continuous perfusion to induce expression of the recombinant blood coagulation factor XI Gly397Ser mutant protein;

(4) performing isolation, purification, filtration, final filling and lyophilization to obtain the expressed highly active blood coagulation factor XI Gly397Ser mutant protein.

In step (3), the serum-free medium is "SAFC Biosciences EX-CELL™ 302" (commercial reagent).

In step (4), the purification comprises primary purification and refined purification.

The present invention additionally provides a plasmid vector expressing the mutant protein (FXI Gly397Ser) for gene transduction. Its preparation and detection include the steps of:

(1) inserting FXI Gly397Ser-encoding cDNA into pcDNA3.1 plasmid containing a CMV promoter;

(2) dissolving 150 µg of a purified plasmid vector expressing FXI Gly397Ser in 2 mL of normal saline, injecting the solution into hemophilia A mice of 4-8 weeks old at a high pressure through caudal vein, and injecting the same volume of PBS as a negative control;

(3) 48 hours after the injection, collecting the orbital blood to detect the blood coagulation factor XI activity with the coagulation APTT method, and to detect the blood coagulation factor XI antigen with the ELISA method;

(4) 72 hours after injection, amputating the tails at the place where the diameter is 2 mm and placing the tails in lukewarm normal saline to observe the bleeding within 10 minutes; estimating the bleeding volume by detecting the amount of hemoglobin, and comparing the bleeding volumes of hemophilia mice transduced with different plasmids after their tails are amputated, on the basis that the bleeding volume is 100% in the buffer injection group;

(5) drawing blood from the heart for thromboelastogram detection.

The highly active blood coagulation factor XI mutant protein is used for preparing a gene therapy drug.

The highly active blood coagulation factor XI mutant protein is used for preparing a recombinant protein therapy drug for the treatment of hemophilia or other hemorrhagic diseases.

The highly active blood coagulation factor XI mutant protein is used for preparing a fusion protein of the blood coagulation factor XI Gly397Ser mutant, and it is applied to a recombinant protein drug for the treatment of hemophilia or other hemorrhagic diseases.

The fusion protein is human albumin, immunoglobulin Fc, transferrin or alpha 1 antitrypsin.

A pharmaceutical composition or gene therapy vector comprising the nucleic acid or amino acid sequence of the present invention is used for diagnosis, prevention and/or treatment of diseases mainly including hemorrhagic diseases or hemorrhage caused by various reasons, among them, the most likely hemorrhagic diseases are hemophilia A and B, i.e. hemorrhagic diseases caused by hereditary blood coagulation factor VIII or IX deficiency, and including hemophilia A and B with inhibitory antibody production, or acquired blood coagulation factor VIII or IX deficiency caused by acquired inhibitor production, and other hemorrhagic diseases to be treated by bypass preparations, such as neonatal coagulopathy, severe liver disease, high-risk surgery, traumatic blood loss, bone marrow transplantation, thrombocytopenia and platelet dysfunction, emergency reversal of oral anticoagulation, congenital blood coagulation factors V, VII, X, and XI deficiency, von Willebrand disease, and acquired von Willebrand disease caused by von Willebrand factor inhibitors, blood loss associated with extensive damage, cerebral hemorrhage, and platelet dysfunction.

BENEFICIAL EFFECTS

The mutant of the present invention has very high blood coagulation activity and stronger capability for catalyzing non-physiological substrates. Thus, it may enhance the blood coagulation activity via a bypass pathway, efficiently activate blood coagulation reaction through a bypass pathway without dependence on the mechanism of blood coagulation factor IX (FIX)/blood coagulation factor VIII (FVIII), improve the body's overall blood coagulation function, and may be used in the treatment of hemorrhagic diseases, with promising prospects in gene therapy and recombinant protein replacement therapy.

BRIEF DESCRIPTION OF THE DRAWINGS

FIG. 1 to FIG. 7 are schematic diagrams of the sequences of nucleic acids and an encoding protein of a highly active blood coagulation factor XI mutant of the present invention. Specifically, FIG. 1 is a schematic diagram of the sequence of nucleic acid as show in SEQ ID NO: 1 and the sequence of encoding protein as show in SEQ ID NO: 7; FIG. 2 is a schematic diagram of the sequence of nucleic acid as show in SEQ ID NO: 2 and the sequence of encoding protein as show in SEQ ID NO: 7; FIG. 3 is a schematic diagram of the sequence of nucleic acid as show in SEQ ID NO: 3 and the sequence of encoding protein as show in SEQ ID NO: 7; FIG. 4 is a schematic diagram of the sequence of nucleic acid as show in SEQ ID NO: 4 and the sequence of encoding protein as show in SEQ ID NO: 7; FIG. 5 is a schematic diagram of the sequence of nucleic acid as show in SEQ ID NO: 5 and the sequence of encoding protein as show in SEQ ID NO: 7; FIG. 6 is a schematic diagram of the sequence of nucleic acid as show in SEQ ID NO: 6 and the sequence of encoding protein as show in SEQ ID NO: 7; FIG. 7 is a schematic diagram of the amino acid sequence of a highly active blood coagulation factor XI mutant protein (FXI G397S) as show in SEQ ID NO: 7 and the amino acid sequence of a wild-type blood coagulation factor XI protein (hFXI) as shown in SEQ ID NO: 8.

FIG. 14a, FIG. 14b, and FIG. 14c are schematic diagrams of thromboelastogram for detecting the gene transduced blood coagulation factor XI mutant Gly397Ser remedying the plasma coagulation deficiency in hemophilia mice, in which FIG. 14a represents a group treated with blood coagulation factor XI mutant Gly397Ser, FIG. 14b represents a group of normal mice without blood coagulation factor VIII deficiency, and FIG. 14c represents a group of hemophilia mice with blood coagulation factor VIII deficiency.

DETAILED DESCRIPTION OF THE INVENTION

Figure 8:
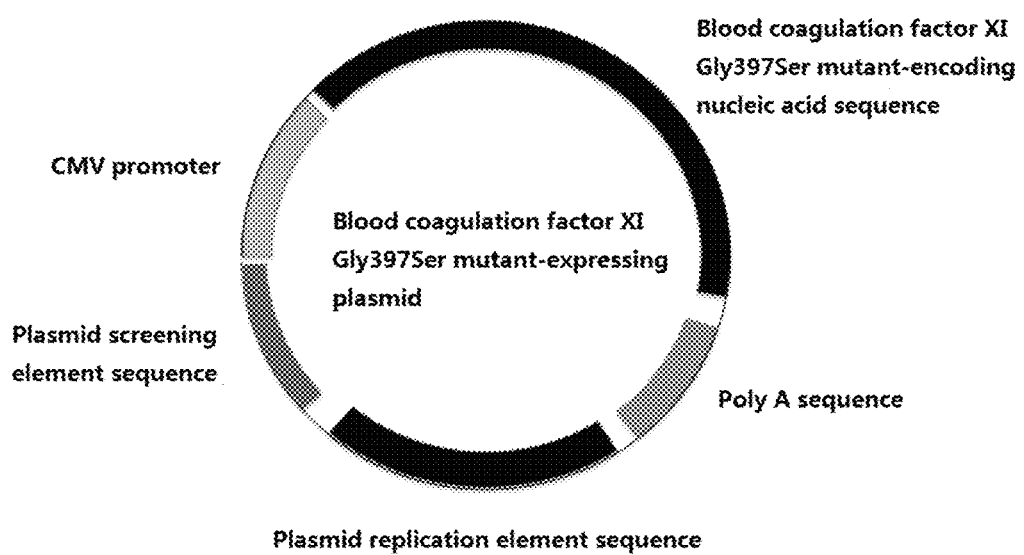
FIG. 8 is a schematic diagram of the vector structure of the present invention.

The present invention is further described below in conjunction with specific Examples. It should be understood that these Examples are only used to illustrate the present invention rather than to limit the scope of the present invention. In addition, it should be understood that, upon reading the disclosure of the present application, persons skilled in the art can make various changes or modifications to the present invention, and these equivalents also fall within the scope defined by the appended claims of the present application.

Example 1

The amino acid sequence of a highly active blood coagulation factor XI mutant protein (FXI G397S) is as shown in SEQ ID NO: 7. The amino acid sequence of a wild-type blood coagulation factor XI protein (hFXI) is as shown in SEQ ID NO: 8.

The method for preparing a highly active blood coagulation factor XI mutant protein includes the steps of:

(1) inserting a human blood coagulation factor IX encoding gene of human wild-type or blood coagulation factor XI mutant Gly397Ser into a vector to obtain a recombinant vector;

(2) transforming a host cell with the above recombinant vector to obtain a recombinant expression cell clone;

(3) cultivating the above cell clone in a serum-free medium to express the highly active blood coagulation factor XI mutant protein;

The serum-free medium was "SAFC Biosciences EX-CELL™ 302" (commercial reagent). In order to ensure product safety and prevent blood-derived preparations from transmitting infectious diseases, a serum-free medium was used for mammalian cell cultivation and protein expression. When the cells reached a steady state after logarithmic growth, the cell density was kept within the target interval for maintaining high expression of blood coagulation factor XI;

(4) performing isolation, purification and lyophilization to obtain the expressed highly active coagulation factor XI mutant protein and relevant fusion protein;

After the medium was collected, it was clarified and filtered by a deep bed filter and further isolated and purified. The purification step was separated into two stages, namely, primary purification and refined purification. The primary purification involved subjecting the filtered and clarified culture solution to 10-fold ultrafiltration concentration, and then inactivating lipid-enveloped viruses such as HIV 1/2, HCV and HBV by an organic solvent/detergent method. The refined purification involved further removing residual impurities mainly composed of other proteins secreted by the host cell from the product with chromatography methods such as ion exchange (anion and cation) and molecular sieve. The purified proteins were subjected to ultrafiltration with the medium changed and the formula adjusted. Then, they were filtered through a 20 nm nanomembrane to remove the viruses, and lyophilized. The lyophilization process involved quick freezing, quenching, freezing, vacuuming, main drying, and post-drying. The lyophilization formula was mainly composed of inert sugars and inorganic salts, such as, glycine, mannitol, sodium chloride, calcium chloride and the like (the components are glycine, mannitol, sodium chloride, calcium chloride, etc.; the time for lyophilization was 30 hours).

Figure 9:
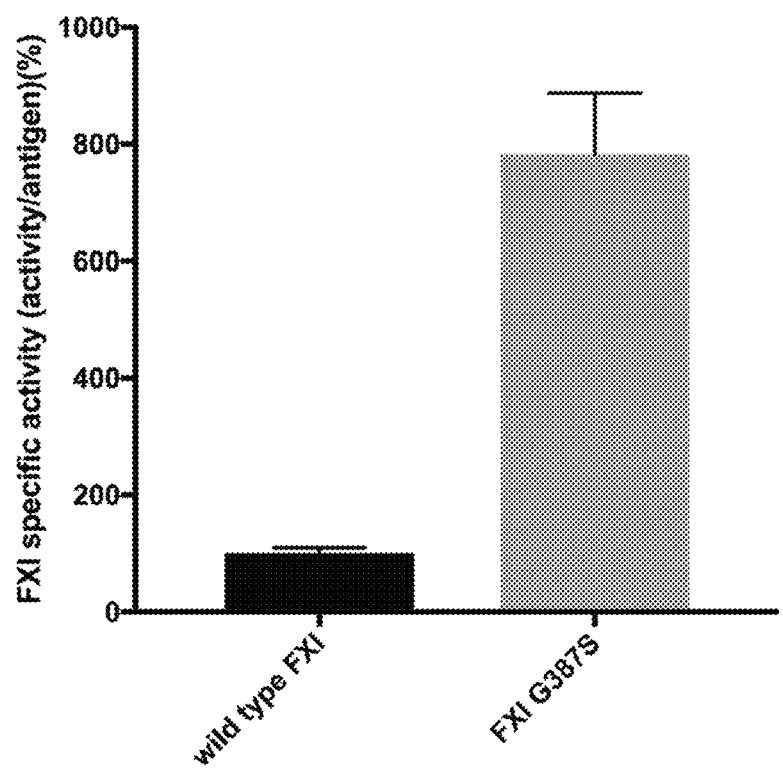
FIG. 9 is a schematic diagram of the activity of the recombinant blood coagulation factor XI mutant Gly397Ser.

(5) Method for detecting the blood coagulation factor XI mutant activity and antigen. The specific blood coagulation activity of the blood coagulation factor XI was deduced by comparing the blood coagulation activity and antigen, see FIG. 9. As illustrated in FIG. 9, the blood coagulation factor XI mutant Gly397Ser exhibited higher blood coagulation activity than the wild type.

Method for detecting the blood coagulation factor XI activity and antigen: ① Detecting the blood coagulation factor XI activity with the coagulation method:

The normally mixed plasma was diluted with OV Buffer at the ratios of 1:10, 1:20, 1:40, 1:80, 1:160, and 1:320 respectively; the plasma sample to be tested was diluted at the ratios of 1:10 and 1:20 respectively; the cell supernatant solution was kept untreated. 50 μl of the diluted normal mixed plasma, the plasma sample to be tested or the cell supernatant solution of the transfected blood coagulation factor XI-expressing vector was added with 50 μl of blood coagulation factor XI substrate plasma, and added with an APTT reagent, incubated at 37° C. for 3 minutes, and then added with 50 μl of calcium chloride. The coagulation time was recorded on the ST4 semi-automatic coagulometer (Stago, France). On the basis that the activity of the blood coagulation factor XI of the normally mixed plasma diluted at the ratio of 1:10 was 100%, a standard curve was established according to the log value of the coagulation time at different dilution rates and the log value of corresponding activity. If the correlation coefficient R2 was greater than 0.95, the value of the sample to be tested would be brought into calculation to obtain the blood coagulation factor XI activity of the sample to be tested.

② Detecting the blood coagulation factor XI antigen with the double-antibody sandwich method:

A coating antibody (F9 ELISA kit, Affinity Biologicals, EIA9-0035R1) was diluted with a coating solution (1.59 g/L sodium carbonate and 2.94 g/L sodium bicarbonate, pH 9.6) at the ratio of 1:100. Then, 100 μl of the diluted antibody was added per well, incubated at room temperature for 2 hours, and washed for 3 times. The normally mixed plasma sample was doubly diluted with a sample dilute (23.8 g HEPES (free acid)/L, 5.84 g/L NaCl, 3.72 g/L Na2EDTA, 10 g/L BSA, 0.1% Tween-20, Ph 7.2) at the ratio from 1:100 until 1:3200. The plasma sample to be tested was diluted at the ratios of 1:200, 1:400 and 1:800, and the cell supernatant was kept as the original solution, and diluted at the ratios of 1:10 and 1:100 respectively. 100 μl of the diluted normally mixed plasma or the sample to be tested was added into each well, left at room temperature for 90 minutes, and washed for 3 times. A detection antibody was diluted with a sample diluent at the ratio of 1:100. Then, 100 μl of the diluted detection antibody was added to each well, left at room temperature for 90 minutes, and washed for 3 times. 100 μl of OPD substrate was added to each well. When a stable yellow color appeared (about 5-10 minutes), 100 μl of a stop solution was added to each well. The absorbance was read with a microplate reader at a wavelength of 450 nm. A standard curve was established and the antigen value of the sample to be tested was calculated.

(6) Using the blood coagulation factor XI mutant to remedy the plasma thrombin generation deficiency in hemophilia A patients Thrombin generation test (TGT): a comprehensive test for monitoring the capability of thrombin generation in plasma. The activator (including a tissue factor and phospholipid) was added into the plasma to initiate the coagulation reaction. Then, a thrombin-specific fluorescent substrate was added. The resulting thrombin-catalyzed substrate released fluorescent groups. The fluorescent signal generated was dynamically monitored by a FLUOROSKAN fluorescence reader, and converted into a thrombin generation curve with a matched thrombin generation lab software. The thrombin generation capability was mainly evaluated by several parameters of the curve: (1) lag time, i.e. the time spanning from the start of reaction to the start of thrombin generation; (2) peak, i.e. the maximum amount of thrombin generated; (3) time to peak (ttpeak), i.e. the time spanning from the start of reaction to the peak of thrombin generation; (4) endogenous thrombin potential (ETP), i.e. the area under the thrombin generation curve, which reflects the total amount of thrombin generated.

Figure 10:
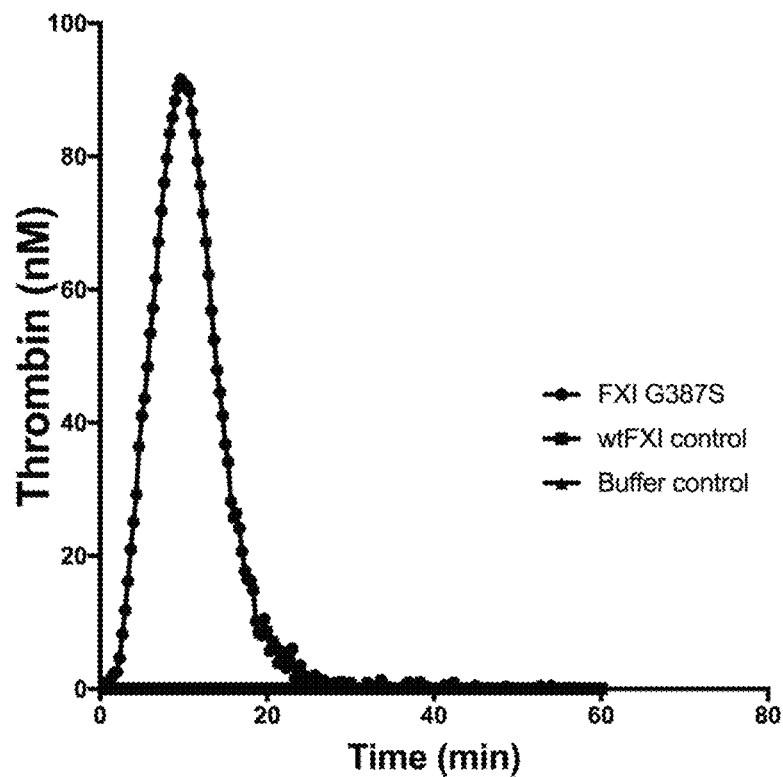
FIG. 10 is a schematic diagram of the plasma thrombin generation via the blood coagulation factor XI mutant Gly397Ser remedying in vitro the blood coagulation factor VIII deficiency.

The blood coagulation factor XI or its mutant (at the concentration of 5 ug/mL normal physiological concentration) was added into the plasma of hemophilia A patients (deficient in blood coagulation factor VIII) to detect the thrombin generation, see FIG. 10. As illustrated in FIG. 10, the blood coagulation factor XI mutant Gly397Ser could partially remedy the thrombin generation disorder caused by blood coagulation factor VIII deficiency.

Example 2

The method for preparing a plasmid vector of the highly active blood coagulation factor XI for gene therapy comprises the steps of:

(1) Constructing a plasmid vector by inserting FXI Gly397Ser-encoding cDNA into pcDNA3.1 plasmid containing a CMV promoter.

(2) Injecting a purified vector into hemophilia A mice. Hemophilia mice of 4-8 weeks old were selected, 6-7 of them were injected with 150 μg of plasmid vector dissolved in 2 mL of normal saline through caudal vein, and 6 of them were injected with PBS as a negative control.

Figure 11:
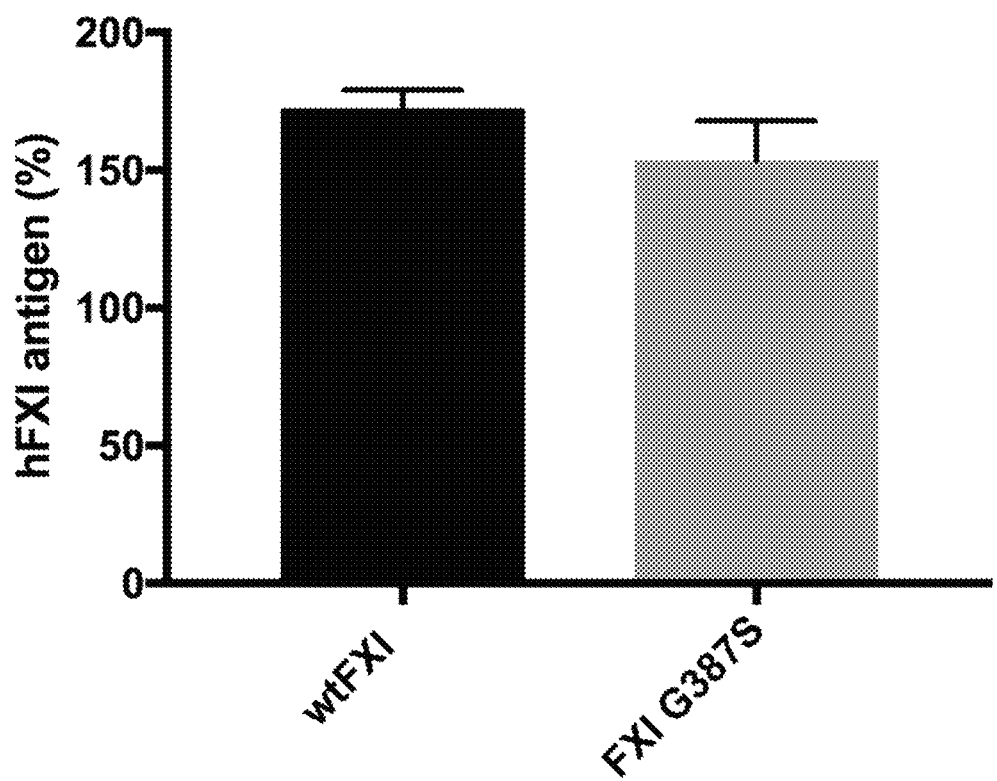
FIG. 11 is a schematic diagram of the human blood coagulation factor XI antigen level in hemophilia mice after gene transduction of the blood coagulation factor XI mutant Gly397Ser.
Figure 12:
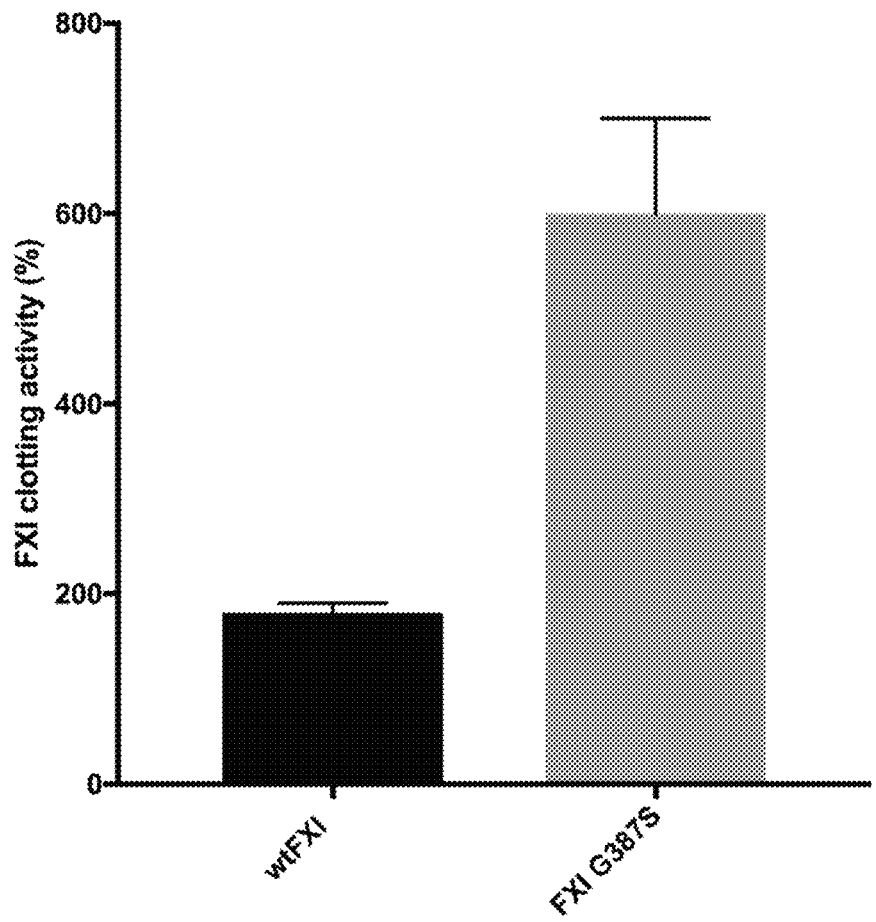
FIG. 12 is a schematic diagram of the activity of the blood coagulation factor XI in hemophilia mice after gene transduction of the blood coagulation factor XI mutant Gly397Ser.

(3) Detecting the blood coagulation factor XI activity with aPTT. 48 hours after the injection, the orbital blood was collected to detect the blood coagulation factor XI activity and antigen, wherein the activity referred to the sum of the activity of the original blood coagulation factor XI in mice and the activity of the human wild-type or mutant blood coagulation factor XI introduced in mice, and the antigen only referred to the level of the human blood coagulation factor XI introduced in mice. The blood coagulation factor XI antigen in mice's plasma after vector gene transduction was shown in FIG. 11. As illustrated in FIG. 11, the expression of blood coagulation factor XI mutant Gly397Ser in the gene-transduced human plasma is similar with the wild-type blood coagulation factor XI. The blood coagulation factor XI activity in mice's plasma after gene transduction of human plasma blood coagulation factor XI mutant Gly397Ser was shown in FIG. 12. As illustrated in FIG. 12, the gene-transduced and expressed human plasma blood coagulation factor XI mutant Gly397Ser exhibited higher blood coagulation activity.

Figure 13:
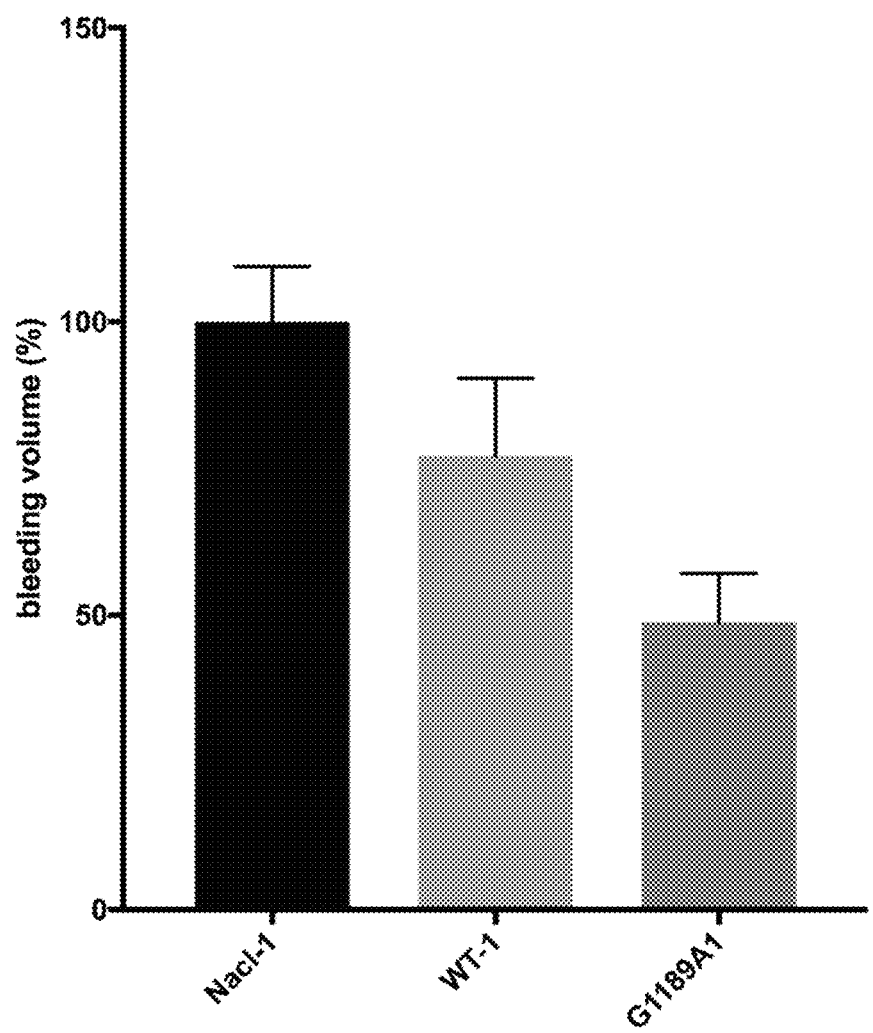
FIG. 13 is a schematic diagram of the bleeding volume of hemophilia mice with tails amputated after gene transduction of the blood coagulation factor XI mutant Gly397Ser.

(4) After the mice were anesthetized, their tails were amputated at the place where the diameter was 2 mm and immersed in PBS. Immediately start time counting for 10 minutes. Then the hemoglobin was detected, and the degree of hemorrhage was estimated according to the amount of hemoglobin (see FIG. 13). As illustrated in FIG. 13, the gene-transfected and expressed human plasma blood coagulation factor XI mutant Gly397Ser could remedy in vivo the blood coagulation deficiency due to blood coagulation factor VIII deficiency, and reduce hemorrhage.

Figure 14A:
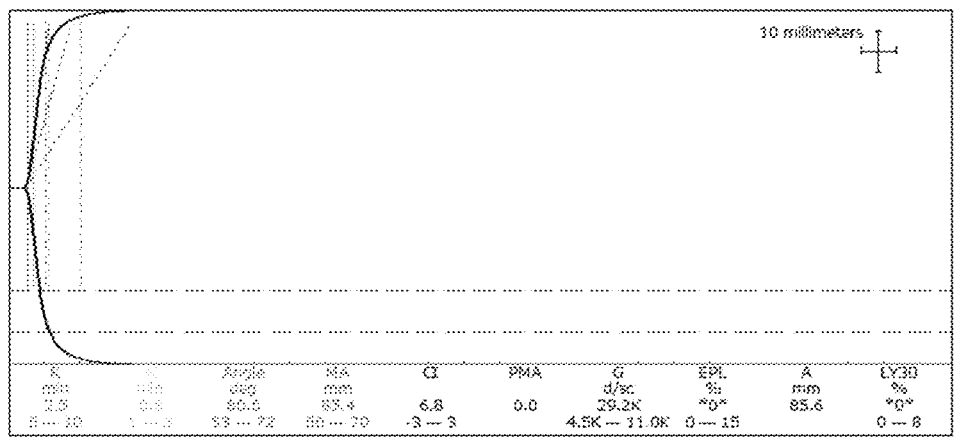
Figure 14B:
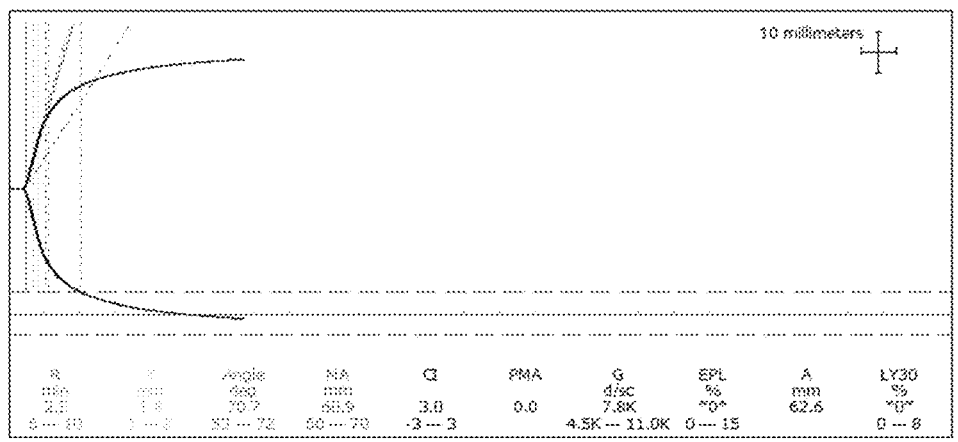
Figure 14C:
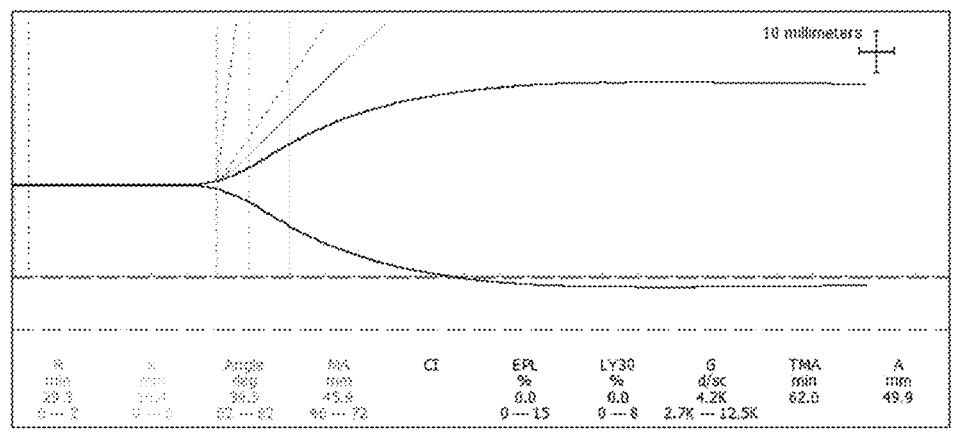

(5) Drawing blood from the heart of mice to detect thromboelasticity (see FIG. 14a to FIG. 14c)

Thromboelastogram (TEG): a comprehensive test for monitoring the entire clotting process of the whole blood. Without processing blood specimens, it can accurately provide the patient's coagulation profile by using a small amount of whole blood to monitor interactions between coagulation factors, platelets, fibrinogen, fibrinolysis system, and other cellular components. During the test, the anticoagulated blood was first added into a reagent bottle for activation monitoring; then a certain volume of the blood was sucked out and added into a special cylindrical cup (pre-added with $CaCl_2$). The cup was rotated at an angle of 4 °45' and a constant speed of 1 round/9s. The coagulation state of the blood was monitored by a needle suspended via a spiral wire and soaked in the blood, and the curve of coagulation speed and intensity was drawn by a computer. The coagulation process was mainly evaluated by the following curve parameters: (1) the reaction time R value, i.e. the time required from the start of detection to the rise of the curve amplitude to 2 mm, which also referred to the time required from the start of specimen detection to the start of fibrin clot formation; (2) the agglutination time K value and the clot formation rate a angle, wherein the agglutination time K value referred to the time required from the end of clotting time to the time when the curve amplitude reached 20 mm, and the clot formation rate a angle referred to the angle between the tangent line from the point of blood clot formation to the maximum arc of the tracing diagram and the horizontal line. They reflected the result of joint action of fibrin and platelets when the blood clot started to form, which was mainly affected by the function of fibrinogen; (3) the MA value which indicated the maximum amplitude of the tracing diagram, i.e. the maximum shear force coefficient. It reflected the strongest kinetic characteristics of the forming fibrin and platelets bonding together and the stability of blood clot formation, wherein the platelets played a greater role than fibrinogen, accounting for about 80%; (4) the coagulation index (CI) value which was deduced in view of the reaction time, agglutination time, clot formation rate, and maximum amplitude in the thromboelastogram curve. It reflected the overall coagulation state of the sample under various conditions, wherein a CI value below −3 indicated low coagulation, a CI value above 3 indicated high coagulation, and a CI value between −3 and 3 indicated normal coagulation.

As illustrated in FIG. 14a to FIG. 14c, the gene-transduced and expressed human plasma blood coagulation factor XI mutant Gly397Ser could remedy in vivo the blood coagulation deficiency due to blood coagulation factor VIII deficiency.

What is claimed is:

1. A highly active blood coagulation factor XI nucleic acid, comprising:
    (1) the nucleotide sequence thereof is as shown in SEQ ID NO: 1, the nucleotide at position 1189 is A rather than G; or
    (2) the nucleotide sequence thereof is as shown in SEQ ID NO: 2, the nucleotide at position 1189 is A rather than G, and the nucleotide at position 1191 is C rather than T; or
    (3) the nucleotide sequence thereof is as shown in SEQ ID NO: 3, the nucleotide at position 1189 is T rather than G, and the nucleotide at position 1190 is C rather than G; or
    (4) the nucleotide sequence thereof is as shown in SEQ ID NO: 4, the nucleotide at position 1189 is T rather than G, the nucleotide at position 1190 is C rather than G, and the nucleotide at position 1191 is C rather than T; or
    (5) the nucleotide sequence thereof is as shown in SEQ ID NO: 5, the nucleotide at position 1189 is T rather than G, the nucleotide at position 1190 is C rather than G, and the nucleotide at position 1191 is A rather than T; or
    (6) the nucleotide sequence thereof is as shown in SEQ ID NO: 6, the nucleotide at position 1189 is T rather than G, the nucleotide at position 1190 is C rather than G, and the nucleotide at position 1191 is G rather than T.

2. A highly active blood coagulation factor XI protein according to claim 1, wherein the amino acid sequence thereof is as shown in SEQ ID NO: 7, the amino acid at position 397 in the mutant (FXI G397S) is Ser rather than Gly in human wild-type FXI (hFXI).

3. A nucleic acid encoding the highly active blood coagulation factor XI protein according to claim 2, or a nucleic acid having the same length as and being completely complementary to the encoding nucleic acid.

4. A vector expressing the highly active blood coagulation factor XI protein according to claim 2.

5. A method for preparing a highly active blood coagulation factor XI protein, comprising the steps of:
    (1) inserting a human coagulation factor XI gene of human blood coagulation factor XI Gly397Ser mutant into a vector to obtain a recombinant vector;
    (2) transforming a host cell with the above recombinant vector to obtain a cell clone expressing the recombinant blood coagulation factor XI Gly397Ser mutant;
    (3) cultivating the above recombinant cell clone in a serum-free medium by continuous perfusion to induce expression of the recombinant blood coagulation factor XI Gly397Ser mutant protein;
    (4) performing isolation, purification, filtration, final filling and lyophilization to obtain the expressed highly active blood coagulation factor XI Gly397Ser mutant protein, wherein the position of the mutation is relative to the wild type human factor XI sequence of SEQ ID NO: 8.

* * * * *

SEQUENCE LISTING

<160> NUMBER OF SEQ ID NOS: 8

<210> SEQ ID NO 1
<211> LENGTH: 1878
<212> TYPE: DNA
<213> ORGANISM: Artificial Sequence
<220> FEATURE:
<223> OTHER INFORMATION: Synthesized

<400> SEQUENCE: 1

| | | | | | | |
|---|---|---|---|---|---|---|
| atgattttct | tatatcaagt | ggtacatttc | attttattta | cttcagtttc | tggtgaatgt | 60 |
| gtgactcagt | tgttgaagga | cacctgcttt | gaaggagggg | acattactac | ggtcttcaca | 120 |
| ccaagcgcca | agtactgcca | ggtagtctgc | acttaccacc | caagatgttt | actcttcact | 180 |
| ttcacggcgg | aatcaccatc | tgaggatccc | acccgatggt | ttacttgtgt | cctgaaagac | 240 |
| agtgttacag | aaacactgcc | aagagtgaat | aggacagcag | cgatttctgg | gtattctttc | 300 |
| aagcaatgct | cacaccaaat | aagcgcttgc | aacaaagaca | tttatgtgga | cctagacatg | 360 |
| aagggcataa | actataacag | ctcagttgcc | aagagtgctc | aagaatgcca | agaaagatgc | 420 |
| acggatgacg | tccactgcca | cttttttcacg | tacgccacaa | ggcagtttcc | cagcctggag | 480 |
| catcgtaaca | tttgtctact | gaagcacacc | caaacaggga | caccaaccag | aataacgaag | 540 |
| ctcgataaag | tggtgtctgg | attttcactg | aaatcctgtg | cactttctaa | tctggcttgt | 600 |
| attagggaca | ttttccctaa | tacggtgttt | gcagacagca | catcgacag | tgtcatggct | 660 |
| cccgatgctt | ttgtctgtgg | ccgaatctgc | actcatcatc | ccggttgctt | gttttttacc | 720 |
| ttcttttccc | aggaatggcc | caaagaatct | caaagaaatc | tttgtctcct | taaaacatct | 780 |
| gagagtggat | tgcccagtac | acgcattaaa | aagagcaaag | ctctttctgg | tttcagtcta | 840 |
| caaagctgca | ggcacagcat | cccagtgttc | tgccattctt | cattttacca | tgacactgat | 900 |
| ttcttgggag | aagaactgga | tattgttgct | gcaaaaagtc | acgaggcctg | ccagaaactg | 960 |
| tgcaccaatg | ccgtccgctg | ccagtttttt | acctataccc | cagcccaagc | atcctgcaac | 1020 |
| gaagggaagg | gcaagtgtta | cttaaagctt | tcttcaaacg | gatctccaac | taaaatactt | 1080 |
| cacgggagag | gaggcatctc | tggatacaca | ttaaggttgt | gtaaaatgga | taatgagtgt | 1140 |
| accaccaaaa | tcaagcccag | gatcgttgga | ggaactgcgt | ctgttcgtag | tgagtggccg | 1200 |
| tggcaggtga | ccctgcacac | aacctcaccc | actcagagac | cctgtgtgg | aggctccatc | 1260 |
| attggaaacc | agtggatatt | aacagccgct | cactgtttct | atggggtaga | gtcacctaag | 1320 |
| attttgcgtg | tctacagtgg | cattttaaat | caatctgaaa | taaagagga | cacatctttc | 1380 |
| tttggggttc | aagaaataat | aatccatgat | cagtataaaa | tggcagaaag | cgggtatgat | 1440 |
| attgccttgt | tgaaactgga | accacagtg | aattacacag | attctcaacg | acccatatgc | 1500 |
| ctgccttcca | aggagatag | aaatgtaata | tacactgatt | gctgggtgac | tggatgggg | 1560 |
| tacagaaaac | taagagacaa | aatacaaaat | actctccaga | aagccaagat | acccttagtg | 1620 |
| accaacgaag | agtgccagaa | gagatacaga | ggacataaaa | taacccataa | gatgatctgt | 1680 |
| gccggctaca | gggaaggagg | gaaggacgct | tgcaagggag | attcgggagg | ccctctgtcc | 1740 |
| tgcaaacaca | atgaggtctg | gcatctggta | ggcatcacga | gctggggcga | aggctgtgct | 1800 |
| caaagggagc | ggccaggtgt | ttacaccaac | gtggtcgagt | acgtggactg | gattctggag | 1860 |
| aaaactcaag | cagtgtga | | | | | 1878 |

<210> SEQ ID NO 2
<211> LENGTH: 1878

```
<212> TYPE: DNA
<213> ORGANISM: Artificial Sequence
<220> FEATURE:
<223> OTHER INFORMATION: Synthesized

<400> SEQUENCE: 2
atgattttct tatatcaagt ggtacatttc attttattta cttcagtttc tggtgaatgt       60
gtgactcagt tgttgaagga cacctgcttt gaaggagggg acattactac ggtcttcaca      120
ccaagcgcca agtactgcca ggtagtctgc acttaccacc caagatgttt actcttcact      180
ttcacggcgg aatcaccatc tgaggatccc acccgatggt ttacttgtgt cctgaaagac      240
agtgttacag aaacactgcc aagagtgaat aggacagcag cgatttctgg gtattctttc      300
aagcaatgct cacaccaaat aagcgcttgc aacaaagaca tttatgtgga cctagacatg      360
aagggcataa actataacag ctcagttgcc aagagtgctc aagaatgcca agaaagatgc      420
acggatgacg tccactgcca cttttcacg tacgccacaa ggcagtttcc cagcctggag      480
catcgtaaca tttgtctact gaagcacacc caaacaggga caccaaccag aataacgaag      540
ctcgataaag tggtgtctgg attttcactg aaatcctgtg cactttctaa tctggcttgt      600
attagggaca ttttccctaa tacggtgttt gcagacagca acatcgacag tgtcatggct      660
cccgatgctt ttgtctgtgg ccgaatctgc actcatcatc ccggttgctt gttttttacc      720
ttcttttccc aggaatggcc caagaatct caaagaaatc tttgtctcct taaaacatct      780
gagagtggat tgcccagtac acgcattaaa aagagcaaag ctctttctgg tttcagtcta      840
caaagctgca ggcacagcat cccagtgttc tgccattctt cattttacca tgacactgat      900
ttcttgggag aagaactgga tattgttgct gcaaaaagtc acgaggcctg ccagaaactg      960
tgcaccaatg ccgtccgctg ccagttttt acctataccc cagcccaagc atcctgcaac     1020
gaagggaagg gcaagtgtta cttaaagctt tcttcaaacg atctccaac taaaatactt     1080 cacgggagag gaggcatctc tggatacaca ttaaggttgt gtaaaatgga taatgagtgt     1140
accaccaaaa tcaagcccag gatcgttgga ggaactgcgt ctgttcgtag cgagtggccg     1200
tggcaggtga ccctgcacac aacctcaccc actcagagac acctgtgtgg aggctccatc     1260
attggaaacc agtggatatt aacagccgct cactgtttct atggggtaga gtcacctaag     1320
attttgcgtg tctacagtgg cattttaaat caatctgaaa taaaagagga cacatctttc     1380
tttggggttc aagaaataat aatccatgat cagtatataaa tggcagaaag cgggtatgat     1440
attgccttgt tgaaactgga aaccacagtg aattacacag attctcaacg acccatatgc     1500
ctgccttcca aaggagatag aaatgtaata tacactgatt gctgggtgac tggatggggg     1560
tacagaaaac taagagacaa aatacaaaat actctccaga aagccaagat acccttagtg     1620
accaacgaag agtgccagaa gagatacaga ggacataaaa taacccataa gatgatctgt     1680
gccggctaca gggaaggagg gaaggacgct tgcaagggag attcgggagg ccctctgtcc     1740
tgcaaacaca atgaggtctg gcatctggta ggcatcacga gctggggcga aggctgtgct     1800
caaagggagc ggccaggtgt ttacaccaac gtggtcgagt acgtggactg gattctggag     1860
aaaactcaag cagtgtga                                                   1878

<210> SEQ ID NO 3
<211> LENGTH: 1878
<212> TYPE: DNA
<213> ORGANISM: Artificial Sequence
<220> FEATURE:
<223> OTHER INFORMATION: Synthesized
```

<400> SEQUENCE: 3

```
atgattttct tatatcaagt ggtacatttc attttattta cttcagtttc tggtgaatgt      60
gtgactcagt tgttgaagga cacctgcttt gaaggagggg acattactac ggtcttcaca     120
ccaagcgcca agtactgcca ggtagtctgc acttaccacc caagatgttt actcttcact     180
ttcacggcgg aatcaccatc tgaggatccc acccgatggt ttacttgtgt cctgaaagac     240
agtgttacag aaacactgcc aagagtgaat aggacagcag cgatttctgg gtattctttc     300
aagcaatgct cacaccaaat aagcgcttgc aacaaagaca tttatgtgga cctagacatg     360
aagggcataa actataacag ctcagttgcc aagagtgctc aagaatgcca agaaagatgc     420
acggatgacg tccactgcca cttttcacg tacgccacaa ggcagtttcc cagcctggag      480
catcgtaaca tttgtctact gaagcacacc caaacaggga caccaaccag ataacgaag      540
ctcgataaag tggtgtctgg attttcactg aaatcctgtg cactttctaa tctggcttgt     600
attagggaca ttttccctaa tacggtgttt gcagacagca acatcgacag tgtcatggct     660
cccgatgctt tgtctgtgg ccgaatctgc actcatcatc ccggttgctt gttttttacc      720
ttcttttccc aggaatggcc caaagaatct caagaaatc tttgtctcct taaaacatct      780
gagagtggat tgcccagtac acgcattaaa agagcaaag ctctttctgg tttcagtcta      840
caaagctgca ggcacagcat cccagtgttc tgccattctt cattttacca tgacactgat     900
ttcttgggag aagaactgga tattgttgct gcaaaaagtc acgaggcctg ccagaaactg     960
tgcaccaatg ccgtccgctg ccagtttttt acctataccc cagcccaagc atcctgcaac    1020
gaagggaagg caagtgtta cttaaagctt tcttcaaacg gatctccaac taaaatactt      1080
cacgggagag gaggcatctc tggatacaca ttaaggttgt gtaaaatgga taatgagtgt    1140
accaccaaaa tcaagcccag gatcgttgga ggaactgcgc tgttcgttc tgagtggccg     1200
tggcaggtga ccctgcacac aacctcaccc actcagagac acctgtgtgg aggctccatc    1260
attgaaaacc agtggatatt aacagccgct cactgttct atggggtaga gtcacctaag     1320
attttgcgtg tctacagtgg cattttaaat caatctgaaa taaagagga cacatctttc     1380
tttggggttc aagaaataat aatccatgat cagtataaaa tggcagaaag cgggtatgat    1440
attgccttgt tgaaactgga accacagtg aattacacag attctcaacg acccatatgc      1500
ctgccttcca aggagatag aaatgtaata tacactgatt gctgggtgac tggatggggg     1560
tacagaaaac taagagacaa aatacaaaat actctccaga aagccaagat acccttagtg    1620
accaacgaag agtgccagaa gagatacaga ggacataaaa taacccataa gatgatctgt    1680
gccggctaca gggaaggagg aaggacgct tgcaagggag attcgggagg ccctctgtcc     1740
tgcaaacaca atgaggtctg gcatctggta ggcatcacga gctggggcga aggctgtgct    1800
caaagggagc ggccaggtgt ttacaccaac gtggtcgagt acgtggactg gattctggag    1860
aaaactcaag cagtgtga                                                  1878
```

<210> SEQ ID NO 4
<211> LENGTH: 1878
<212> TYPE: DNA
<213> ORGANISM: Artificial Sequence
<220> FEATURE:
<223> OTHER INFORMATION: Synthesized

<400> SEQUENCE: 4

```
atgattttct tatatcaagt ggtacatttc attttattta cttcagtttc tggtgaatgt      60
gtgactcagt tgttgaagga cacctgcttt gaaggagggg acattactac ggtcttcaca     120
```

```
ccaagcgcca agtactgcca ggtagtctgc acttaccacc caagatgttt actcttcact    180
ttcacggcgg aatcaccatc tgaggatccc acccgatggt ttacttgtgt cctgaaagac    240
agtgttacag aaacactgcc aagagtgaat aggacagcag cgatttctgg gtattctttc    300
aagcaatgct cacaccaaat aagcgcttgc aacaaagaca tttatgtgga cctagacatg    360
aagggcataa actataacag ctcagttgcc aagagtgctc aagaatgcca agaaagatgc    420
acggatgacc tccactgcca ctttttcacg tacgccacaa ggcagtttcc cagcctggag    480
catcgtaaca tttgtctact gaagcacacc caaacaggga caccaaccag aataacgaag    540
ctcgataaag tggtgtctgg attttcactg aaatcctgtg cactttctaa tctggcttgt    600
attagggaca ttttccctaa tacggtgttt gcagacagca catcgacag tgtcatggct     660 cccgatgctt ttgtctgtgg ccgaatctgc actcatcatc ccggttgctt gttttttacc    720
ttcttttccc aggaatggcc caaagaatct caaagaaatc tttgtctcct taaaacatct    780
gagagtggat tgcccagtac acgcattaaa aagagcaaag ctctttctgg tttcagtcta    840
caaagctgca ggcacagcat cccagtgttc tgccattctt cattttacca tgacactgat    900
ttcttgggag aagaactgga tattgttgct gcaaaaagtc acgaggcctg ccagaaactg    960
tgcaccaatg ccgtccgctg ccagtttttt acctataccc cagcccaagc atcctgcaac   1020
gaagggaagg gcaagtgtta cttaaagctt tcttcaaacg gatctccaac taaaatactt   1080
cacgggagag gaggcatctc tggatacaca ttaaggttgt gtaaaatgga taatgagtgt   1140
accaccaaaa tcaagcccag gatcgttgga ggaactgcgt ctgttcgttc cgagtggccg   1200
tggcaggtga ccctgcacac aacctcaccc actcagagac cctgtgtgg aggctccatc    1260 attggaaacc agtggatatt aacagccgct cactgtttct atggggtaga gtcacctaag   1320
attttgcgtg tctacagtgg cattttaaat caatctgaaa taaagagga cacatctttc    1380 tttggggttc aagaaataat aatccatgat cagtataaaa tggcagaaag cgggtatgat   1440
attgccttgt tgaaactgga accacagtg aattacacag attctcaacg acccatatgc    1500 ctgcccttcca aaggagatag aaatgtaata tacactgatt gctgggtgac tggatggggg   1560
tacagaaaac taagagacaa aatacaaaat actctccaga aagccaagat acccttagtg   1620
accaacgaag agtgccagaa agatacaga ggacataaaa taacccataa gatgatctgt    1680
gccggctaca gggaaggagg gaaggacgct tgcaagggag attcgggagg ccctctgtcc   1740
tgcaaacaca atgaggtctg gcatctggta ggcatcacga gctggggcga aggctgtgct    1800
caaagggagc ggccaggtgt ttacaccaac gtggtcgagt acgtggactg gattctggag    1860
aaaactcaag cagtgtga                                                  1878
```

<210> SEQ ID NO 5
<211> LENGTH: 1878
<212> TYPE: DNA
<213> ORGANISM: Artificial Sequence
<220> FEATURE:
<223> OTHER INFORMATION: Synthesized

<400> SEQUENCE: 5

```
atgattttct tatatcaagt ggtacatttc attttattta cttcagtttc tggtgaatgt     60
gtgactcagt tgttgaagga cacctgcttt gaaggagggg acattactac ggtcttcaca    120
ccaagcgcca agtactgcca ggtagtctgc acttaccacc caagatgttt actcttcact    180
ttcacggcgg aatcaccatc tgaggatccc acccgatggt ttacttgtgt cctgaaagac    240
```

| | |
|---|---:|
| agtgttacag aaacactgcc aagagtgaat aggacagcag cgatttctgg gtattctttc | 300 |
| aagcaatgct cacaccaaat aagcgcttgc aacaaagaca tttatgtgga cctagacatg | 360 |
| aagggcataa actataacag ctcagttgcc aagagtgctc aagaatgcca agaaagatgc | 420 |
| acggatgacg tccactgcca cttttcacg tacgccacaa ggcagtttcc cagcctggag | 480 |
| catcgtaaca tttgtctact gaagcacacc caaacaggga caccaaccag aataacgaag | 540 |
| ctcgataaag tggtgtctgg atttcactg aaatcctgtg cactttctaa tctggcttgt | 600 |
| attagggaca ttttccctaa tacggtgttt gcagacagca catcgacag tgtcatggct | 660 |
| cccgatgctt tgtctgtgg ccgaatctgc actcatcatc ccggttgctt gttttttacc | 720 |
| ttctttcc aggaatggcc caaagaatct caaagaaatc tttgtctcct taaaacatct | 780 |
| gagagtggat tgcccagtac acgcattaaa aagagcaaag ctctttctgg tttcagtcta | 840 |
| caaagctgca ggcacagcat cccagtgttc tgccattctt catttaccaa tgacactgat | 900 |
| ttcttgggag aagaactgga tattgttgct gcaaaaagtc acgaggcctg ccagaaactg | 960 |
| tgcaccaatg ccgtccgctg ccagttttt acctatatccc cagcccaagc atcctgcaac | 1020 |
| gaagggaagg gcaagtgtta cttaaagctt tcttcaaacg gatctccaac taaatactt | 1080 |
| cacgggagag gaggcatctc tggatacaca ttaaggttgt gtaaaatgga taatgagtgt | 1140 |
| accaccaaaa tcaagcccag gatcgttgga ggaactgcgt ctgttcgttc agagtggccg | 1200 |
| tggcaggtga ccctgcacac aacctcaccc actcagagac acctgtgtgg aggctccatc | 1260 |
| attggaaacc agtggatatt aacagccgct cactgtttct atggggtaga gtcacctaag | 1320 |
| attttgcgtg tctacagtgg cattttaaat caatctgaaa taaaagagga cacatctttc | 1380 |
| tttggggttc aagaaataat aatccatgat cagtataaaa tggcagaaag cgggtatgat | 1440 |
| attgccttgt tgaaactgga aaccacagtg aattacacag attctcaacg acccatatgc | 1500 |
| ctgccttcca aggagatag aaatgtaata tacactgatt gctgggtgac tggatggggg | 1560 |
| tacagaaaac taagagacaa aatacaaaat actctccaga aagccaagat acccttagtg | 1620 |
| accaacgaag agtgccagaa gagatacaga ggacataaaa taacccataa gatgatctgt | 1680 |
| gccggctaca gggaaggagg gaaggacgct tgcaagggag attcgggagg ccctctgtcc | 1740 |
| tgcaaacaca atgaggtctg gcatctggta ggcatcacga gctgggcga aggctgtgct | 1800 |
| caaagggagc ggccaggtgt ttacaccaac gtggtcgagt acgtggactg gattctggag | 1860 |
| aaaactcaag cagtgtga | 1878 |

<210> SEQ ID NO 6
<211> LENGTH: 1878
<212> TYPE: DNA
<213> ORGANISM: Artificial Sequence
<220> FEATURE:
<223> OTHER INFORMATION: Synthesized

<400> SEQUENCE: 6

| | |
|---|---:|
| atgattttct tatatcaagt ggtacatttc atttatttta cttcagtttc tggtgaatgt | 60 |
| gtgactcagt tgttgaagga cacctgcttt gaaggagggg acattactac ggtcttcaca | 120 |
| ccaagcgcca agtactgcca ggtagtctgc acttaccacc caagatgttt actcttcact | 180 |
| ttcacggcgg aataccatc tgaggatccc acccgatggt ttacttgtgt cctgaaagac | 240 |
| agtgttacag aaacactgcc aagagtgaat aggacagcag cgatttctgg gtattctttc | 300 |
| aagcaatgct cacaccaaat aagcgcttgc aacaaagaca tttatgtgga cctagacatg | 360 |
| aagggcataa actataacag ctcagttgcc aagagtgctc aagaatgcca agaaagatgc | 420 |

-continued

```
acggatgacg tccactgcca cttttttcacg tacgccacaa ggcagtttcc cagcctggag    480
catcgtaaca tttgtctact gaagcacacc caaacaggga caccaaccag aataacgaag    540
ctcgataaag tggtgtctgg attttcactg aaatcctgtg cactttctaa tctggcttgt    600
attagggaca ttttccctaa tacggtgttt gcagacagca acatcgacag tgtcatggct    660
cccgatgctt tgtctgtgg ccgaatctgc actcatcatc ccggttgctt gttttttacc    720
ttcttttccc aggaatggcc caaagaatct caaagaaatc tttgtctcct taaaacatct    780
gagagtggat tgcccagtac acgcattaaa aagagcaaag ctctttctgg tttcagtcta    840
caaagctgca ggcacagcat cccagtgttc tgccattctt cattttacca tgacactgat    900
ttcttgggag aagaactgga tattgttgct gcaaaaagtc acgaggcctg ccagaaactg    960
tgcaccaatg ccgtccgctg ccagtttttt acctatatccc cagcccaagc atcctgcaac   1020
gaagggaagg gcaagtgtta cttaaagctt tcttcaaacg gatctccaac taaaatactt   1080
cacgggagag gaggcatctc tggatacaca ttaaggttgt gtaaaatgga taatgagtgt   1140
accaccaaaa tcaagcccag gatcgttgga ggaactgcgt ctgttcgttc ggagtggccg   1200
tggcaggtga ccctgcacac aacctcaccc actcagagac acctgtgtgg aggctccatc   1260
attggaaacc agtggatatt aacagccgct cactgtttct atggggtaga gtcacctaag   1320
attttgcgtg tctacagtgg cattttaaat caatctgaaa taaaagagga cacatctttc   1380
tttggggttc aagaaataat aatccatgat cagtataaaa tggcagaaag cgggtatgat   1440
attgccttgt tgaaactgga aaccacagtg aattacacag attctcaacg acccatatgc   1500
ctgccttcca aaggagatag aaatgtaata tacactgatt gctgggtgac tggatggggg   1560
tacagaaaac taagagacaa aatacaaaat actctccaga aagccaagat acccttagtg   1620
accaacgaag agtgccagaa gagatacaga ggacataaaa taacccataa gatgatctgt   1680
gccggctaca gggaaggagg gaaggacgct tgcaagggag attcgggagg ccctctgtcc   1740
tgcaaacaca atgaggtctg gcatctggta ggcatcacga gctggggcga aggctgtgct   1800
caaagggagc ggccaggtgt ttacaccaac gtggtcgagt acgtggactg gattctggag   1860
aaaactcaag cagtgtga                                                  1878
```

<210> SEQ ID NO 7
<211> LENGTH: 625
<212> TYPE: PRT
<213> ORGANISM: Artificial Sequence
<220> FEATURE:
<223> OTHER INFORMATION: Synthesized

<400> SEQUENCE: 7

```
Met Ile Phe Leu Tyr Gln Val Val His Phe Ile Leu Phe Thr Ser Val
1               5                   10                  15

Ser Gly Glu Cys Val Thr Gln Leu Leu Lys Asp Thr Cys Phe Glu Gly
                20                  25                  30

Gly Asp Ile Thr Thr Val Phe Thr Pro Ser Ala Lys Tyr Cys Gln Val
            35                  40                  45

Val Cys Thr Tyr His Pro Arg Cys Leu Leu Phe Thr Phe Thr Ala Glu
        50                  55                  60

Ser Pro Ser Glu Asp Pro Thr Arg Trp Phe Thr Cys Val Leu Lys Asp
65                  70                  75                  80

Ser Val Thr Glu Thr Leu Pro Arg Val Asn Arg Thr Ala Ala Ile Ser
                85                  90                  95
```

-continued

```
Gly Tyr Ser Phe Lys Gln Cys Ser His Gln Ile Ser Ala Cys Asn Lys
            100                 105                 110

Asp Ile Tyr Val Asp Leu Asp Met Lys Gly Ile Asn Tyr Asn Ser Ser
        115                 120                 125

Val Ala Lys Ser Ala Gln Glu Cys Gln Glu Arg Cys Thr Asp Asp Val
    130                 135                 140

His Cys His Phe Phe Thr Tyr Ala Thr Arg Gln Phe Pro Ser Leu Glu
145                 150                 155                 160

His Arg Asn Ile Cys Leu Leu Lys His Thr Gln Thr Gly Thr Pro Thr
                165                 170                 175

Arg Ile Thr Lys Leu Asp Lys Val Val Ser Gly Phe Ser Leu Lys Ser
            180                 185                 190

Cys Ala Leu Ser Asn Leu Ala Cys Ile Arg Asp Ile Phe Pro Asn Thr
        195                 200                 205

Val Phe Ala Asp Ser Asn Ile Asp Ser Val Met Ala Pro Asp Ala Phe
    210                 215                 220

Val Cys Gly Arg Ile Cys Thr His His Pro Gly Cys Leu Phe Phe Thr
225                 230                 235                 240

Phe Phe Ser Gln Glu Trp Pro Lys Glu Ser Gln Arg Asn Leu Cys Leu
                245                 250                 255

Leu Lys Thr Ser Glu Ser Gly Leu Pro Ser Thr Arg Ile Lys Lys Ser
            260                 265                 270

Lys Ala Leu Ser Gly Phe Ser Leu Gln Ser Cys Arg His Ser Ile Pro
        275                 280                 285

Val Phe Cys His Ser Ser Phe Tyr His Asp Thr Asp Phe Leu Gly Glu
    290                 295                 300

Glu Leu Asp Ile Val Ala Ala Lys Ser His Glu Ala Cys Gln Lys Leu
305                 310                 315                 320

Cys Thr Asn Ala Val Arg Cys Gln Phe Phe Thr Tyr Thr Pro Ala Gln
                325                 330                 335

Ala Ser Cys Asn Glu Gly Lys Gly Lys Cys Tyr Leu Lys Leu Ser Ser
            340                 345                 350

Asn Gly Ser Pro Thr Lys Ile Leu His Gly Arg Gly Gly Ile Ser Gly
        355                 360                 365

Tyr Thr Leu Arg Leu Cys Lys Met Asp Asn Glu Cys Thr Thr Lys Ile
    370                 375                 380

Lys Pro Arg Ile Val Gly Gly Thr Ala Ser Val Arg Ser Glu Trp Pro
385                 390                 395                 400

Trp Gln Val Thr Leu His Thr Thr Ser Pro Thr Gln Arg His Leu Cys
                405                 410                 415

Gly Gly Ser Ile Ile Gly Asn Gln Trp Ile Leu Thr Ala Ala His Cys
            420                 425                 430

Phe Tyr Gly Val Glu Ser Pro Lys Ile Leu Arg Val Tyr Ser Gly Ile
        435                 440                 445

Leu Asn Gln Ser Glu Ile Lys Glu Asp Thr Ser Phe Phe Gly Val Gln
    450                 455                 460

Glu Ile Ile Ile His Asp Gln Tyr Lys Met Ala Glu Ser Gly Tyr Asp
465                 470                 475                 480

Ile Ala Leu Leu Lys Leu Glu Thr Thr Val Asn Tyr Thr Asp Ser Gln
                485                 490                 495

Arg Pro Ile Cys Leu Pro Ser Lys Gly Asp Arg Asn Val Ile Tyr Thr
            500                 505                 510

Asp Cys Trp Val Thr Gly Trp Gly Tyr Arg Lys Leu Arg Asp Lys Ile
```

```
                515                 520                 525
Gln Asn Thr Leu Gln Lys Ala Lys Ile Pro Leu Val Thr Asn Glu Glu
            530                 535                 540
Cys Gln Lys Arg Tyr Arg Gly His Lys Ile Thr His Lys Met Ile Cys
545                 550                 555                 560
Ala Gly Tyr Arg Glu Gly Gly Lys Asp Ala Cys Lys Gly Asp Ser Gly
                565                 570                 575
Gly Pro Leu Ser Cys Lys His Asn Glu Val Trp His Leu Val Gly Ile
            580                 585                 590
Thr Ser Trp Gly Glu Gly Cys Ala Gln Arg Glu Arg Pro Gly Val Tyr
                595                 600                 605
Thr Asn Val Val Glu Tyr Val Asp Trp Ile Leu Glu Lys Thr Gln Ala
            610                 615                 620
Val
625

<210> SEQ ID NO 8
<211> LENGTH: 625
<212> TYPE: PRT
<213> ORGANISM: Homo sapiens

<400> SEQUENCE: 8

Met Ile Phe Leu Tyr Gln Val Val His Phe Ile Leu Phe Thr Ser Val
1               5                   10                  15
Ser Gly Glu Cys Val Thr Gln Leu Leu Lys Asp Thr Cys Phe Glu Gly
                20                  25                  30
Gly Asp Ile Thr Thr Val Phe Thr Pro Ser Ala Lys Tyr Cys Gln Val
            35                  40                  45
Val Cys Thr Tyr His Pro Arg Cys Leu Leu Phe Thr Phe Thr Ala Glu
        50                  55                  60
Ser Pro Ser Glu Asp Pro Thr Arg Trp Phe Thr Cys Val Leu Lys Asp
65                  70                  75                  80
Ser Val Thr Glu Thr Leu Pro Arg Val Asn Arg Thr Ala Ala Ile Ser
                85                  90                  95
Gly Tyr Ser Phe Lys Gln Cys Ser His Gln Ile Ser Ala Cys Asn Lys
                100                 105                 110
Asp Ile Tyr Val Asp Leu Asp Met Lys Gly Ile Asn Tyr Asn Ser Ser
            115                 120                 125
Val Ala Lys Ser Ala Gln Glu Cys Gln Glu Arg Cys Thr Asp Asp Val
        130                 135                 140
His Cys His Phe Phe Thr Tyr Ala Thr Arg Gln Phe Pro Ser Leu Glu
145                 150                 155                 160
His Arg Asn Ile Cys Leu Leu Lys His Thr Gln Thr Gly Thr Pro Thr
                165                 170                 175
Arg Ile Thr Lys Leu Asp Lys Val Val Ser Gly Phe Ser Leu Lys Ser
            180                 185                 190
Cys Ala Leu Ser Asn Leu Ala Cys Ile Arg Asp Ile Phe Pro Asn Thr
        195                 200                 205
Val Phe Ala Asp Ser Asn Ile Asp Ser Val Met Ala Pro Asp Ala Phe
    210                 215                 220
Val Cys Gly Arg Ile Cys Thr His His Pro Gly Cys Leu Phe Phe Thr
225                 230                 235                 240
Phe Phe Ser Gln Glu Trp Pro Lys Glu Ser Gln Arg Asn Leu Cys Leu
                245                 250                 255
```

```
Leu Lys Thr Ser Glu Ser Gly Leu Pro Ser Thr Arg Ile Lys Lys Ser
            260                 265                 270

Lys Ala Leu Ser Gly Phe Ser Leu Gln Ser Cys Arg His Ser Ile Pro
            275                 280                 285

Val Phe Cys His Ser Ser Phe Tyr His Asp Thr Asp Phe Leu Gly Glu
            290                 295                 300

Glu Leu Asp Ile Val Ala Ala Lys Ser His Glu Ala Cys Gln Lys Leu
305                 310                 315                 320

Cys Thr Asn Ala Val Arg Cys Gln Phe Phe Thr Tyr Thr Pro Ala Gln
                325                 330                 335

Ala Ser Cys Asn Glu Gly Lys Gly Lys Cys Tyr Leu Lys Leu Ser Ser
            340                 345                 350

Asn Gly Ser Pro Thr Lys Ile Leu His Gly Arg Gly Gly Ile Ser Gly
            355                 360                 365

Tyr Thr Leu Arg Leu Cys Lys Met Asp Asn Glu Cys Thr Thr Lys Ile
            370                 375                 380

Lys Pro Arg Ile Val Gly Gly Thr Ala Ser Val Arg Gly Glu Trp Pro
385                 390                 395                 400

Trp Gln Val Thr Leu His Thr Thr Ser Pro Thr Gln Arg His Leu Cys
                405                 410                 415

Gly Gly Ser Ile Ile Gly Asn Gln Trp Ile Leu Thr Ala Ala His Cys
            420                 425                 430

Phe Tyr Gly Val Glu Ser Pro Lys Ile Leu Arg Val Tyr Ser Gly Ile
            435                 440                 445

Leu Asn Gln Ser Glu Ile Lys Glu Asp Thr Ser Phe Phe Gly Val Gln
            450                 455                 460

Glu Ile Ile Ile His Asp Gln Tyr Lys Met Ala Glu Ser Gly Tyr Asp
465                 470                 475                 480

Ile Ala Leu Leu Lys Leu Glu Thr Thr Val Asn Tyr Thr Asp Ser Gln
                485                 490                 495

Arg Pro Ile Cys Leu Pro Ser Lys Gly Asp Arg Asn Val Ile Tyr Thr
            500                 505                 510

Asp Cys Trp Val Thr Gly Trp Gly Tyr Arg Lys Leu Arg Asp Lys Ile
            515                 520                 525

Gln Asn Thr Leu Gln Lys Ala Lys Ile Pro Leu Val Thr Asn Glu Glu
            530                 535                 540

Cys Gln Lys Arg Tyr Arg Gly His Lys Ile Thr His Lys Met Ile Cys
545                 550                 555                 560

Ala Gly Tyr Arg Glu Gly Gly Lys Asp Ala Cys Lys Gly Asp Ser Gly
                565                 570                 575

Gly Pro Leu Ser Cys Lys His Asn Glu Val Trp His Leu Val Gly Ile
            580                 585                 590

Thr Ser Trp Gly Glu Gly Cys Ala Gln Arg Glu Arg Pro Gly Val Tyr
            595                 600                 605

Thr Asn Val Val Glu Tyr Val Asp Trp Ile Leu Glu Lys Thr Gln Ala
            610                 615                 620

Val
625
```